US009445082B2

(12) United States Patent
Tsukagoshi et al.

(10) Patent No.: US 9,445,082 B2
(45) Date of Patent: Sep. 13, 2016

(54) SYSTEM, APPARATUS, AND METHOD FOR IMAGE PROCESSING

(71) Applicant: Toshiba Medical Systems Corporation, Otawara-shi (JP)

(72) Inventors: Shinsuke Tsukagoshi, Nasushiobara (JP); Satoshi Wakai, Nasushiobara (JP); Yoshiyuki Kokojima, Yokohama (JP); Go Mukumoto, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 222 days.

(21) Appl. No.: 14/039,936

(22) Filed: Sep. 27, 2013

(65) Prior Publication Data
US 2014/0028669 A1 Jan. 30, 2014

Related U.S. Application Data

(63) Continuation of application No. PCT/JP2012/059200, filed on Apr. 4, 2012.

(30) Foreign Application Priority Data

Apr. 7, 2011 (JP) ................................ 2011-085838

(51) Int. Cl.
*G06T 15/00* (2011.01)
*H04N 13/04* (2006.01)
(Continued)

(52) U.S. Cl.
CPC ........... *H04N 13/0429* (2013.01); *A61B 6/022* (2013.01); *A61B 6/462* (2013.01);
(Continued)

(58) Field of Classification Search
CPC ....... G06T 19/00; G06T 17/20; G06T 17/00; G06T 15/10; G06T 15/00
USPC .......................................................... 345/419
See application file for complete search history.

(56) References Cited

U.S. PATENT DOCUMENTS

| 6,760,020 B1 | 7/2004 | Uchiyama et al. |
| 7,567,648 B2 * | 7/2009 | Tsubaki ................. A61B 6/022 378/41 |

(Continued)

FOREIGN PATENT DOCUMENTS

| JP | 9-186957 | 7/1997 |
| JP | 2000-020757 A | 1/2000 |

(Continued)

OTHER PUBLICATIONS

International Search Report issued Jul. 3, 2012 in PCT/JP2012/059200 filed on Apr. 4, 2012.

(Continued)

*Primary Examiner* — Ke Xiao
*Assistant Examiner* — Gordon Liu
(74) *Attorney, Agent, or Firm* — Oblon, McClelland, Maier & Neustadt, L.L.P

(57) ABSTRACT

According to one embodiment, an image processing system includes a stereoscopic display device and an image processing apparatus. The stereoscopic display device is configured to enable a stereoscopic image constituted by using a predetermined parallax number of parallax images to be stereoscopically viewed. The image processing apparatus comprises a rendering processor configured to apply rendering processing to volume data serving as three-dimensional medical image data, a rendering processing controller configured to control the rendering processor so as to generate from the volume data a parallax image group composed of the predetermined parallax number or more of parallax images, and a storage controller configured to store in a memory the parallax image group generated by the rendering processor. The stereoscopic display device is configured to display the stereoscopic image constituted by selecting the predetermined parallax number of parallax images out of the parallax image group stored in the memory.

16 Claims, 27 Drawing Sheets

(51) Int. Cl.
| | |
|---|---|
| *H04N 13/02* | (2006.01) |
| *A61B 6/02* | (2006.01) |
| *A61B 6/00* | (2006.01) |
| *A61B 8/00* | (2006.01) |
| *A61B 8/08* | (2006.01) |
| *G09G 3/00* | (2006.01) |

(52) U.S. Cl.
CPC .............. *A61B 6/466* (2013.01); *A61B 8/466* (2013.01); *A61B 8/483* (2013.01); *H04N 13/0275* (2013.01); *H04N 13/0278* (2013.01); *H04N 13/0282* (2013.01); *A61B 6/503* (2013.01); *A61B 6/5211* (2013.01); *A61B 8/0883* (2013.01); *G09G 3/003* (2013.01); *G09G 2380/08* (2013.01)

(56) References Cited

U.S. PATENT DOCUMENTS

| | | | | |
|---|---|---|---|---|
| 8,924,864 | B2* | 12/2014 | Mariotti | G06F 19/321 715/753 |
| 2001/0010730 | A1* | 8/2001 | Rhoads | G06F 21/445 382/100 |
| 2004/0066555 | A1 | 4/2004 | Nomura | |
| 2005/0083246 | A1 | 4/2005 | Saishu et al. | |
| 2005/0148848 | A1 | 7/2005 | Guang et al. | |
| 2011/0043615 | A1 | 2/2011 | Saishu et al. | |
| 2012/0139911 | A1 | 6/2012 | Saishu et al. | |
| 2012/0327186 | A1* | 12/2012 | Kitamura | A61B 1/00009 348/45 |

FOREIGN PATENT DOCUMENTS

| | | |
|---|---|---|
| JP | 2003-348621 A | 12/2003 |
| JP | 2004-126902 A | 4/2004 |
| JP | 2005-086414 A | 3/2005 |
| JP | 2006-101329 A | 4/2006 |
| JP | 2007-531554 A | 11/2007 |
| JP | 2010-250457 A | 11/2010 |

OTHER PUBLICATIONS

Office Action issued Jan. 22, 2013 in Japanese Patent Application No. 2011-085838 filed on Apr. 7, 2011 (with English Translation).

Office Action issued Apr. 21, 2015 in Japanese Patent Application No. 2012-281813.

Office Action and Search Report issued on Feb. 28, 2015 in the corresponding Chinese Patent Application No. 201280000565.9 (with translation of category of cited documents).

* cited by examiner

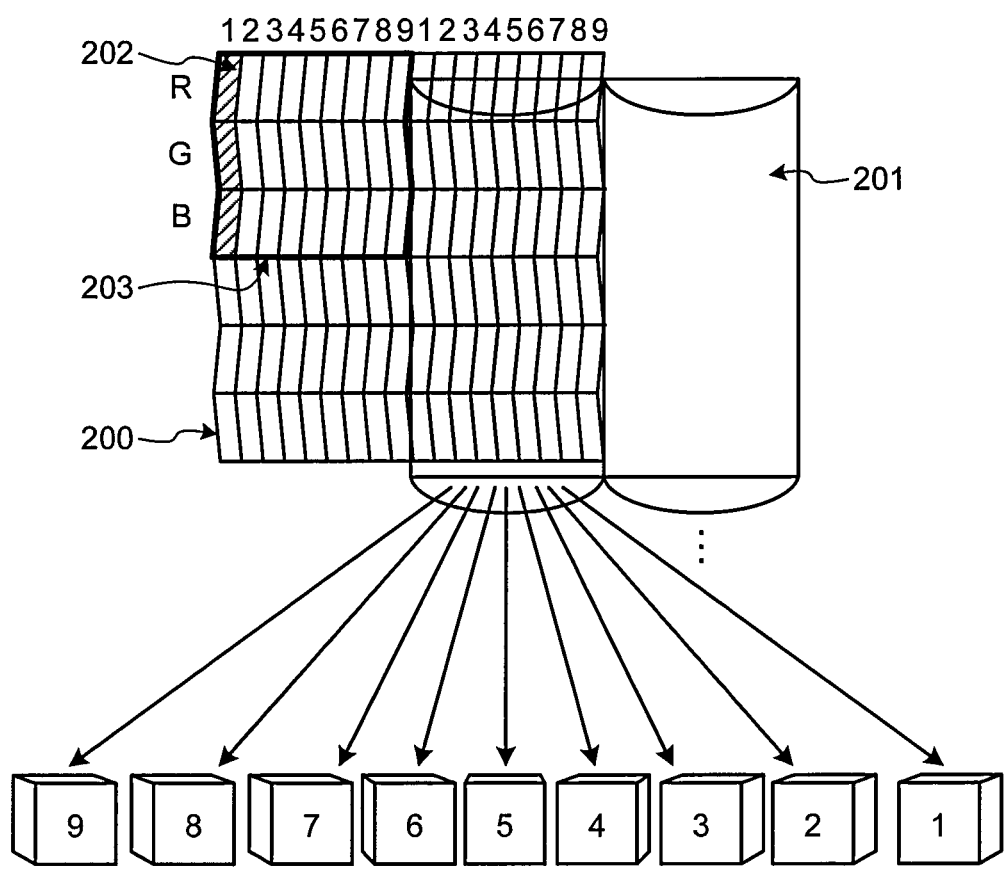

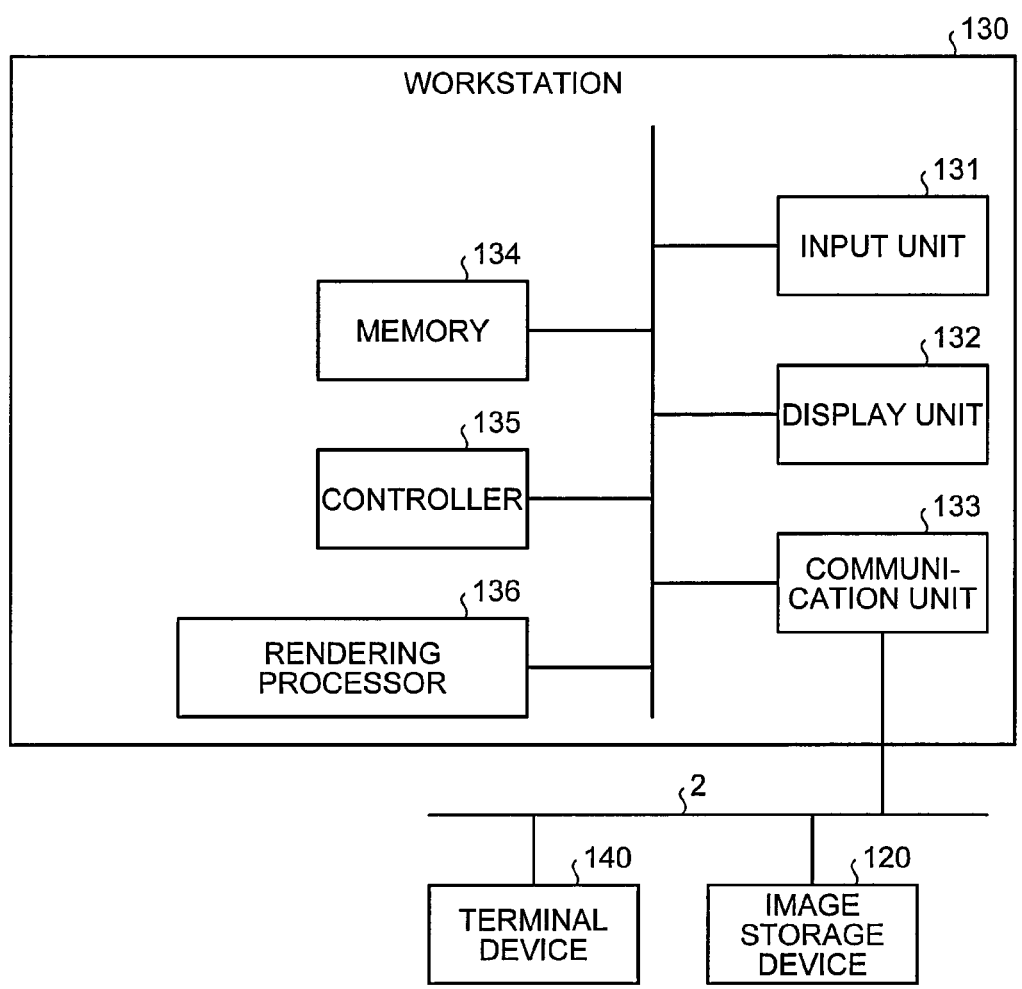

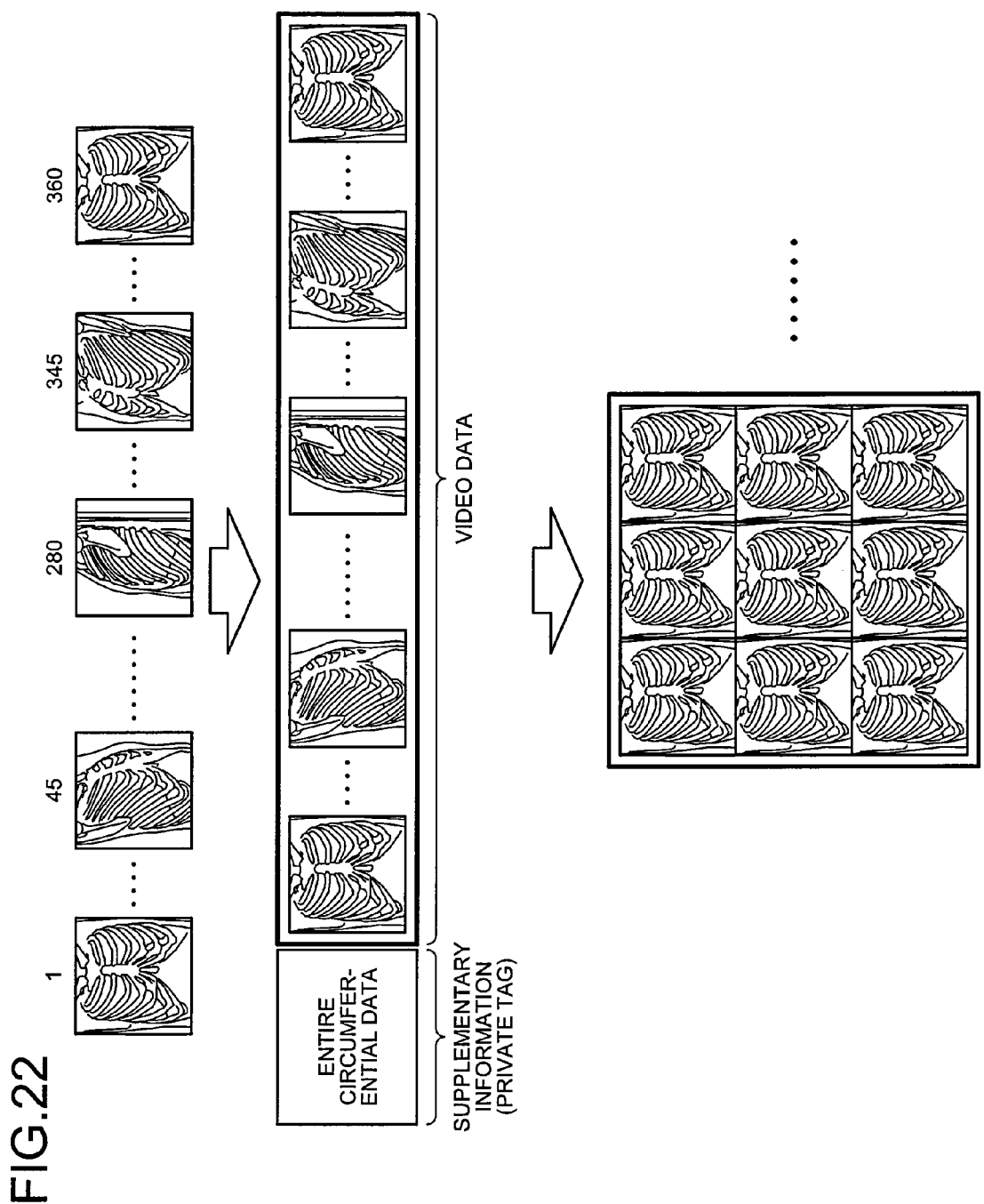

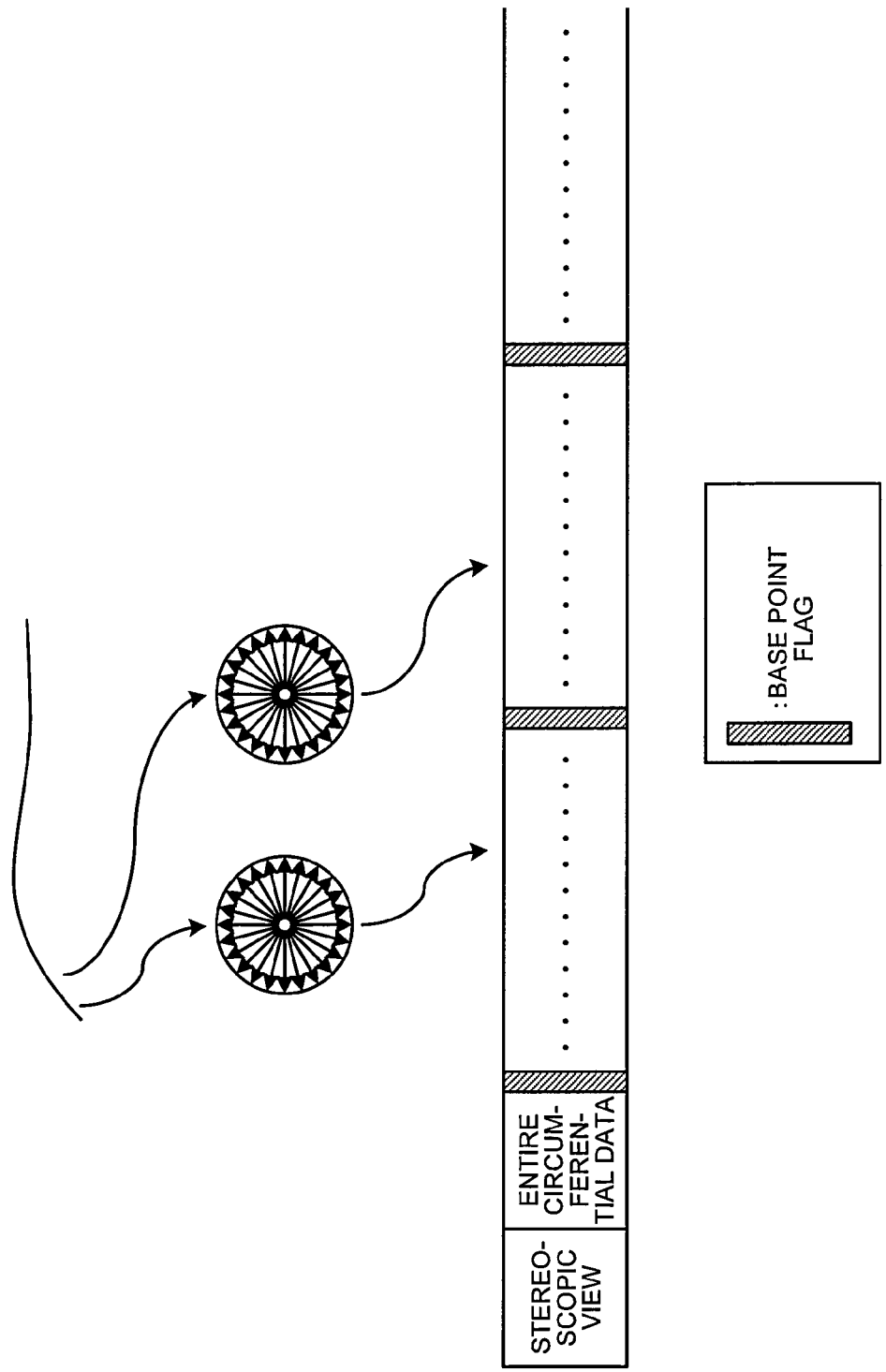

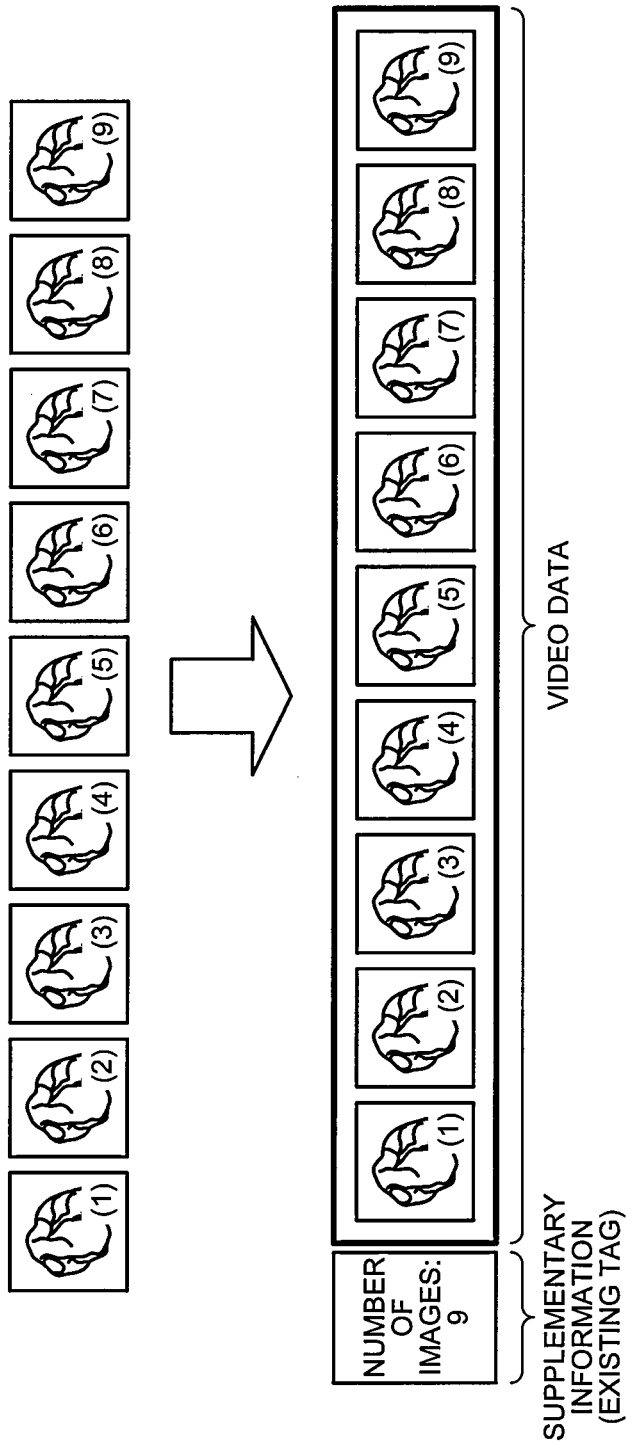

SYSTEM, APPARATUS, AND METHOD FOR IMAGE PROCESSING

CROSS-REFERENCE TO RELATED APPLICATIONS

This application is a continuation of PCT international application Ser. No. PCT/JP2012/059200 filed on Apr. 4, 2012 which designates the United States, incorporated herein by reference, and which claims the benefit of priority from Japanese Patent Applications No. 2011-085838, filed on Apr. 7, 2011, incorporated herein by reference.

FIELD

Embodiments described herein relate generally to a system, an apparatus, and a method for image processing.

BACKGROUND

Conventionally, monitors are in practical use that enable a two-parallax image photographed from two viewpoints to be stereoscopically viewed by using a special instrument such as eyeglasses for stereoscopic viewing. In recent years, monitors are also in practical use that enable, by using a light beam controller such as a lenticular lens, a multi-parallax image (such as a nine-parallax image) photographed from a plurality of viewpoints to be stereoscopically viewed by naked eyes. There are also cases in which depth information of an image photographed from one viewpoint is estimated, and the estimate information is used in image processing to generate the two-parallax image or the nine-parallax image to be displayed on the stereoscopically viewable monitor.

There are practically used medical diagnostic imaging apparatuses, such as an X-ray computed tomography (CT) apparatus, a magnetic resonance imaging (MRI) apparatus, and an ultrasonic diagnostic apparatus, that can generate three-dimensional medical image data (hereinafter called volume data). From the volume data generated by the medical diagnostic imaging apparatus, a volume rendering images (parallax images) having arbitrary parallax number at arbitrary parallax angles can be generated. Accordingly, it is studied to stereoscopically display the two-dimensional volume rendering image generated from the volume data on a stereoscopically viewable monitor that has been practically used in recent years.

However, in order to perform the volume rendering processing in real-time in response to a request from an operator, the apparatus performing the volume rendering processing is required to have a high image processing capacity.

BRIEF DESCRIPTION OF THE DRAWINGS

FIG. 3 is a diagram for explaining an example of a stereoscopic display monitor that performs stereoscopic display by using a nine-parallax image;

FIG. 4 is a diagram for explaining a configuration example of a workstation according to the first embodiment;

FIG. 21A, FIG. 21B, FIG. 22, and FIG. 23 are diagrams for explaining a private tag attached to video data;

FIG. 24 and FIG. 25 are diagrams for explaining DICOM standard compliant supplementary information attached to the video data;

DETAILED DESCRIPTION

According to one embodiment, an image processing system includes a stereoscopic display device and an image processing apparatus. The stereoscopic display device is configured to enable a stereoscopic image constituted by using a predetermined parallax number of parallax images to be stereoscopically viewed. The image processing apparatus comprises a rendering processor configured to apply rendering processing to volume data serving as three-dimensional medical image data, a rendering processing controller configured to control the rendering processor so as to generate from the volume data a parallax image group composed of the predetermined parallax number or more of parallax images, and a storage controller configured to store in a memory the parallax image group generated by the rendering processor. The stereoscopic display device is configured to display the stereoscopic image constituted by selecting the predetermined parallax number of parallax images out of the parallax image group stored in the memory.

Embodiments of an image processing system will be described below in detail with reference to the accompanying drawings. The terms used in the embodiments to be described below are explained as follows. The term "parallax image" refers to an individual image constituting a "stereoscopic image". That is, a "stereoscopic image" is constituted by a plurality of "parallax images" having different "parallax angles" from each other. The term "parallax number" refers to the number of "parallax images" required for being stereoscopically viewed on a stereoscopic display monitor. The term "parallax angle" refers to an angle determined by distances between positions of viewpoints set for generating the "stereoscopic image" and by a position of volume data. The term "nine-parallax image" to be described later refers to a "stereoscopic image" constituted by nine "parallax images". The term "two-parallax image" to be described later refers to a "stereoscopic image" constituted by two "parallax images".

Figure 1:
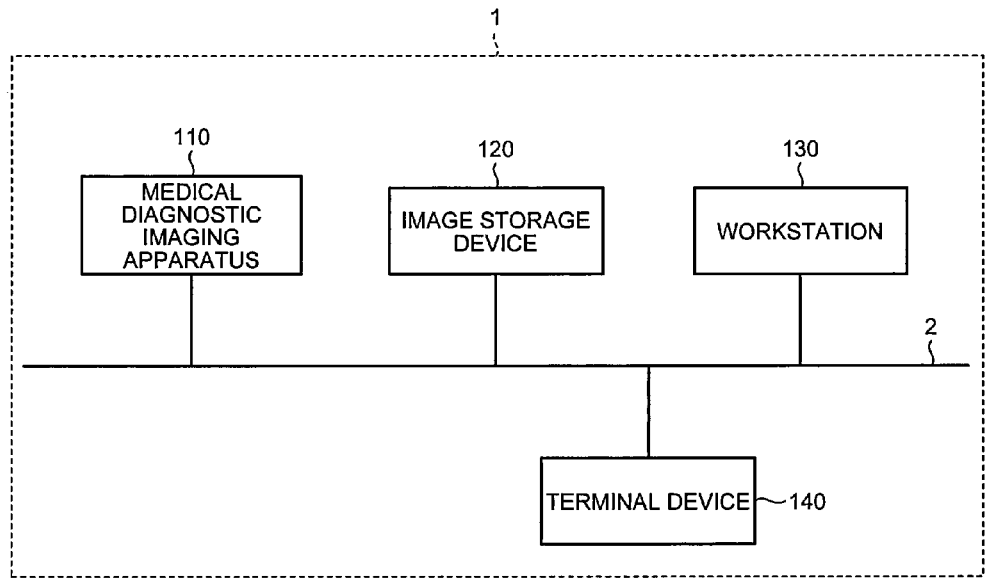
FIG. 1 is a diagram for explaining a configuration example of an image processing system according to a first embodiment.

First, a configuration example of the image processing system according to a first embodiment will be described. FIG. 1 is a diagram for explaining the configuration example of the image processing system according to the first embodiment.

As illustrated in FIG. 1, an image processing system 1 includes a medical diagnostic imaging apparatus 110, an image storage device 120, a workstation 130, and a terminal device 140. The devices illustrated in FIG. 1 are directly or indirectly communicable with each other, for example, via an in-hospital local area network (LAN) 2 installed in a hospital. For example, if a picture archiving and communication system (PACS) is introduced in the image processing system 1, the devices send and receive medical images and the like to and from each other in accordance with the Digital Imaging and Communications in Medicine (DICOM) standard.

The image processing system 1 such as described above generates a parallax image group that is usable as a stereoscopic image from volume data serving as three-dimensional medical image data generated by the medical diagnostic imaging apparatus 110, and displays a stereoscopic image constituted by selection from the parallax image group on a stereoscopically viewable monitor, thus providing a stereoscopically viewable medical image for medical doctors and inspection engineers working in the hospital. Here, the stereoscopic image generally refers to a plurality of images that are photographed from a plurality of viewpoints and that have different parallax angles from each other. In the first embodiment, the workstation 130 applies various types of image processing to the volume data and generates the parallax image group. Also, in the first embodiment, the workstation 130 and the terminal device 140 have respective stereoscopically viewable monitors, and display on the monitors the stereoscopic image that is constituted by selection from the parallax image group generated in the workstation 130. The image storage device 120 stores the volume data generated in the medical diagnostic imaging apparatus 110 and the parallax image group generated in the workstation 130. More specifically, the workstation 130 and the terminal device 140 obtain the volume data and the parallax image group from the image storage device 120, and process and display on the monitors the obtained data. The devices will be described below in sequence.

The medical diagnostic imaging apparatus 110 is, for example, an X-ray diagnostic apparatus, an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus in which a SPECT apparatus and an X-ray CT apparatus are integrated with each other, a PET-CT apparatus in which a PET apparatus and an X-ray CT apparatus are integrated with each other, or a group of these apparatuses. The medical diagnostic imaging apparatus 110 according to the first embodiment can generate the three-dimensional medical image data (volume data).

Specifically, the medical diagnostic imaging apparatus 110 according to the first embodiment generates the volume data by photographing a subject. For example, the medical diagnostic imaging apparatus 110 collects data, such as projection data or MR signals, by photographing the subject, and from the collected data, reconstructs medical images in a plurality of axial planes along the direction of the body axis of the subject, thereby generating the volume data. The medical diagnostic imaging apparatus 110 reconstructs, for example, medical images in 500 axial planes. This group of the medical images in the 500 axial planes constitutes the volume data. The volume data may also be constituted by the data itself, such as projection data or MR signals, of the subject photographed by the medical diagnostic imaging apparatus 110.

The medical diagnostic imaging apparatus 110 also sends the generated volume data to the image storage device 120. When sending the volume data to the image storage device 120, the medical diagnostic imaging apparatus 110 sends, as supplementary information, for example, a patient ID identifying a patient, an inspection ID identifying an inspection, an apparatus ID identifying the medical diagnostic imaging apparatus 110, and a series ID identifying one shot of photographing by the medical diagnostic imaging apparatus 110.

The image storage device 120 is a database that stores the medical images. Specifically, the image storage device 120 according to the first embodiment stores the volume data sent from the medical diagnostic imaging apparatus 110 in a memory and stores the volume data there. In addition, in the first embodiment, the workstation 130 generates the parallax image group from the volume data, and sends the generated parallax image group to the image storage device 120. The image storage device 120 stores the parallax image group sent from the workstation 130 in the memory, and stores the parallax image group there. The present embodiment may be a case in which the workstation 130 and the image storage device 120 illustrated in FIG. 1 are integrated with each other by using a type of the workstation 130 that can store large-capacity images. In other words, the present embodiment may be a case in which the workstation 130 itself stores the volume data or the parallax image group.

In the first embodiment, the volume data and the parallax image group are stored in a corresponding manner to, for example, the patient ID, the inspection ID, the apparatus ID, and the series ID. The workstation 130 and the terminal device 140 obtain the volume data or the parallax image group required by an operator from the image storage device 120 by performing a search using, for example, the patient ID, the inspection ID, the apparatus ID, and the series ID entered by the operator.

The workstation 130 is an image processing apparatus that applies image processing to the medical image. Specifically, the workstation 130 according to the first embodiment applies various types of rendering processing to the volume data obtained from the image storage device 120, and generates the parallax image group. The parallax image group refers to a plurality of images having different parallax angles from each other, and, for example, a stereoscopic image displayed on a monitor that enables a nine-parallax image to be stereoscopically viewed by naked eyes refers to nine images (parallax images) having different parallax angles from each other.

The workstation 130 according to the first embodiment includes as a display unit the stereoscopically viewable monitor (hereinafter called stereoscopic display monitor). The workstation 130 generates the parallax image group, and displays the generated parallax image group on the stereoscopic display monitor. As a result, the operator of the workstation 130 can perform operations for generating the parallax image group while checking the stereoscopically viewable medical image displayed on the stereoscopic display monitor.

The workstation 130 also sends the generated parallax image group to the image storage device 120. When sending the parallax image group to the image storage device 120, the workstation 130 additionally sends, as supplementary information, for example, the patient ID, the inspection ID, the apparatus ID, and the series ID. The supplementary information sent when the parallax image group is sent to the image storage device 120 includes also supplementary information related to the parallax image group. The supplementary information related to the parallax image group includes, for example, the number of parallax images (such as 9) and a resolution (such as 466×350 pixels).

The terminal device 140 is a device for allowing the medical doctors and the inspection engineers working in the hospital to view the medical images. The terminal device 140 is, for example, a personal computer (PC), a tablet PC, a personal digital assistant (PDA), or a cellular phone that is operated by the medical doctors and the inspection engineers working in the hospital. Specifically, the terminal device 140 according to the first embodiment includes a stereoscopic display monitor as a display unit. The terminal device 140 obtains the parallax image group from the image storage device 120, and displays on the stereoscopic display monitor the obtained parallax image group or the stereoscopic image constituted by selection from the obtained parallax image group. As a result, the medical doctor or the inspection engineer acting as an observer can view the stereoscopically viewable medical image.

Here, the stereoscopic display monitor included in each of the workstation 130 and the terminal device 140 will be described. An ordinary general-purpose monitor that is currently most commonly used displays two-dimensional images in two dimensions, and cannot display the two-dimensional images stereoscopically. If an observer desires to view a stereoscopic image on the general-purpose monitor, an apparatus that outputs the image to the general-purpose monitor needs to use a parallel method or an intersection method to display, in a parallel manner, two parallax images that are stereoscopically viewable by the observer. Alternatively, the apparatus that outputs the image to the general-purpose monitor needs to display images that are stereoscopically viewable by the observer with a complementary color method by using eyeglasses that have a red cellophane film attached to a portion for the left eye and a blue cellophane film attached to a portion for the right eye.

On the other hand, there is a stereoscopic display monitor that enables the two-parallax image (also called "binocular parallax image") to be stereoscopically viewed by using a special instrument such as eyeglasses for stereoscopic viewing.

Figure 2A:
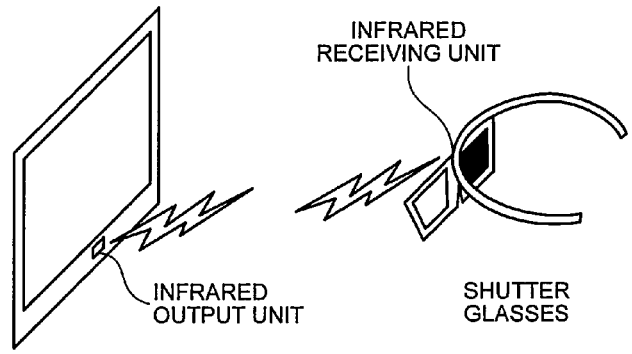
FIG. 2A and FIG. 2B are views for explaining an example of a stereoscopic display monitor that performs stereoscopic display by using a two-parallax image.
Figure 2B:
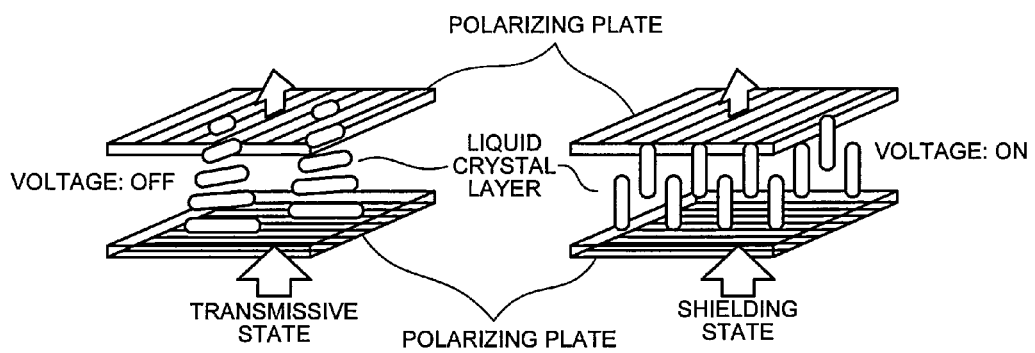

FIGS. 2A and 2B are views for explaining an example of a stereoscopic display monitor that performs stereoscopic display by using a two-parallax image. The example illustrated in FIGS. 2A and 2B is a stereoscopic display monitor that performs the stereoscopic display by using a shutter method, in which shutter glasses are used as the eyeglasses for stereoscopic viewing worn by the observer who observes the monitor. Such a stereoscopic display monitor alternately outputs two parallax images on the monitor. For example, the monitor illustrated in FIG. 2A alternately outputs an image for the left eye and an image for the right eye at 120 Hz. Here, as illustrated in FIG. 2A, an infrared output unit is installed on the monitor, and controls output of an infrared ray in accordance with the timing of switching of the images.

The outgoing infrared ray from the infrared output unit is received by an infrared receiving unit of the shutter glasses illustrated in FIG. 2A. A shutter is mounted at each of right and left frames of the shutter glasses, which switches the right and left shutters alternately between a transmissive state and a shielding state in accordance with the timing of receiving the infrared ray by the infrared receiving unit. The switching process between the transmissive state and the shielding state in the shutters will be described below.

As illustrated in FIG. 2B, each of the shutters has a polarizing plate on the incident side and a polarizing plate on the exit side, and also has a liquid crystal layer between the incident side polarizing plate and the exit side polarizing plate. The incident side polarizing plate and the exit side polarizing plate are perpendicular to each other as illustrated in FIG. 2B. Here, as illustrated in FIG. 2B, in the state of OFF in which no voltage is applied, the light that has passed through the incident side polarizing plate is rotated by 90 degrees by an effect of the liquid crystal layer, and then, passes through the exit side polarizing plate. In other words, the shutter to which no voltage is applied is placed in the transmissive state.

On the other hand, as illustrated in FIG. 2B, in the state of ON in which a voltage is applied, the light that has passed through the incident side polarizing plate is shielded by the exit side polarizing plate because a polarization rotation effect by liquid crystal molecules in the liquid crystal layer disappears. In other words, the shutter to which a voltage is applied is placed in the shielding state.

Accordingly, the infrared output unit, for example, outputs the infrared ray during a period while the image for the left eye is displayed on the monitor. Then, during the period while receiving the infrared ray, the infrared receiving unit applies a voltage to the shutter for the right eye without applying a voltage to the shutter for the left eye. With this operation, as illustrated in FIG. 2A, the image for the left eye enters the observer's left eye because the shutter for the right eye is placed in the shielding state while the shutter for the left eye is placed in the transmissive state. On the other hand, the infrared output unit stops outputting the infrared ray during a period while the image for the right eye is displayed on the monitor. Then, during the period while not receiving the infrared ray, the infrared receiving unit applies a voltage to the shutter for the left eye without applying a voltage to the shutter for the right eye. With this operation, the image for the right eye enters the observer's right eye because the shutter for the left eye is placed in the shielding state while the shutter for the right eye is placed in the transmissive state. In this manner, the stereoscopic display monitor illustrated in FIGS. 2A and 2B displays the images that are stereoscopically viewable by the observer by switching the images and the states of the shutters in conjunction with each other. Note that, as a stereoscopic display monitor that enables a two-parallax image to be stereoscopically viewed, there is also known, in addition to the monitor employing the shutter method described above, a monitor that employs a polarized glasses method.

Moreover, as a stereoscopic display monitor that has been brought into practical use in recent years, there is a monitor that enables a multi-parallax image, such as the nine-parallax image, to be stereoscopically viewed by the observer with naked eyes by using a light beam controller such as a lenticular lens. Such a stereoscopic display monitor enables stereoscopic viewing by binocular parallax, and further enables stereoscopic viewing by motion parallax in which an observed video image changes in accordance with movement of the viewpoint of the observer.

FIG. 3 is a diagram for explaining an example of a stereoscopic display monitor that performs a stereoscopic display by using a nine-parallax image. The stereoscopic display monitor illustrated in FIG. 3 is arranged with a light beam controller on the front surface of a flat display surface 200 such as a liquid crystal panel. For example, in the stereoscopic display monitor illustrated in FIG. 3, a vertical lenticular sheet 201 with optical apertures extending in the vertical direction is stuck as the light beam controller on the front surface of the flat display surface 200. In the example illustrated in FIG. 3, the vertical lenticular sheet 201 is stuck so that convex parts thereof serve as a front surface. However, the example may be a case in which the vertical lenticular sheet 201 is stuck so that the convex parts thereof face the display surface 200.

As illustrated in FIG. 3, the display surface 200 is arranged in a matrix configuration with pixels 202, each of which has an aspect ratio of 3 to 1 and is arranged in the vertical direction with three subpixels of red (R), green (G), and blue(B). The stereoscopic display monitor illustrated in FIG. 3 converts the nine-parallax image constituted by nine images into an intermediate image in which the nine images are arranged in a predetermined format (such as a grid pattern), and then, outputs the intermediate image to the display surface 200. In other words, the stereoscopic display monitor illustrated in FIG. 3 allocates nine pixels located in the same position in the nine-parallax image to respective nine columns of the pixels 202, and outputs the nine columns. The nine columns of the pixels 202 form a unit pixel group 203 that displays nine images having different parallax angles from each other at the same time.

The nine-parallax image that is simultaneously output as the unit pixel group 203 on the display surface 200 is emitted as parallel light, for example, by a light-emitting diode (LED) backlight, and further, radiated in multiple directions by the vertical lenticular sheet 201. Because the light of the pixels of the nine-parallax image is radiated in multiple directions, the light entering the right eye and the left eye of the observer changes in conjunction with the position (position of viewpoint) of the observer. That is, the parallax image entering the right eye and the parallax image entering the left eye have different parallax angles from each other depending on the angle of view of the observer. For this reason, the observer can stereoscopically view a photographed object, for example, in each of the nine positions illustrated in FIG. 3. Furthermore, the observer can for example stereoscopically view, in a position 5 illustrated in FIG. 3, the photographed object in the state of directly facing the photographed object, and can stereoscopically view, in each position other than the position 5 illustrated in FIG. 3, the photographed object in the state in which the direction of the photographed object is changed. Note that the stereoscopic display monitor illustrated in FIG. 3 is merely an example. There may be a case in which the stereoscopic display monitor displaying the nine-parallax image is, as illustrated in FIG. 3, a horizontal stripe liquid crystal display arranged "RRR . . . , GGG . . . , BBB . . . " or a vertical stripe liquid crystal display arranged "RGBRGB . . . ". In addition, there may be a case in which the stereoscopic display monitor illustrated in FIG. 3 is, as illustrated in FIG. 3, a vertical lens type in which the lenticular sheet is a vertical, or a slanted lens type in which the lenticular sheet is slanted.

So far, the configuration example of the image processing system 1 according to the first embodiment has been briefly described. Note that the image processing system 1 described above is not limited to the case in which the PACS is introduced therein. For example, there may be a case in which an electronic chart system that manages electronic charts attached with medical images is introduced in the image processing system 1. In this case, the image storage device 120 is a database that stores the electronic charts. Moreover, there may be a case in which a hospital information system (HIS) or a radiology information system (RIS) is introduced in the image processing system 1. Also, the image processing system 1 is not limited to the above-described configuration example. The functions included in the devices and distribution thereof may be changed as appropriate depending on the mode of operations.

Next, a configuration example of the workstation 130 according to the first embodiment will be described using FIG. 4. FIG. 4 is a diagram for explaining the configuration example of the workstation according to the first embodiment. The terms used below are explained anew as follows. The term "stereoscopic image" refers to an image group for stereoscopic viewing that is generated by applying volume rendering processing to volume data. The term "parallax image" refers to an individual image constituting the "stereoscopic image". That is, the "stereoscopic image" is constituted by a plurality of "parallax images" having different "parallax angles" from each other. The term "parallax number" refers to the number of "parallax images" required for being stereoscopically viewed on the stereoscopic display monitor. The term "parallax angle" refers to an angle determined by distances between positions of viewpoints set for generating the "stereoscopic image" and by a position of volume data. The term "nine-parallax image" to be described later refers to a "stereoscopic image" constituted by nine "parallax images". The term "two-parallax image" to be described later refers to a "stereoscopic image" constituted by two "parallax images".

The workstation 130 according to the first embodiment is a high-performance computer suitable for image processing, and as illustrated in FIG. 4, includes an input unit 131, a display unit 132, a communication unit 133, a memory 134, a controller 135, and a rendering processor 136.

The input unit 131 includes, for example, a mouse, a keyboard, and a trackball, and accepts input of various operations for the workstation 130 from the operator. Specifically, the input unit 131 according to the first embodiment accepts input of information for obtaining volume data to be subjected to the rendering processing from the image storage device 120. For example, the input unit 131 accepts input of, for example, the patient ID, the inspection ID, the apparatus ID, and the series ID. The input unit 131 according to the first embodiment also accepts input of conditions related to the rendering processing (hereinafter called rendering conditions).

The display unit 132 is, for example, a liquid crystal panel serving as the stereoscopic display monitor, and displays various types of information. Specifically, the display unit 132 according to the first embodiment displays graphical user interfaces (GUIs) for accepting various operations from the operator, and stereoscopic images. For example, the display unit 132 is the stereoscopic display monitor described using FIG. 2 (hereinafter mentioned as two-parallax monitor), or a stereoscopic display monitor described using FIG. 5 (hereinafter mentioned as nine-parallax monitor). Description will be made below of the case in which the display unit 132 is the nine-parallax monitor.

The communication unit 133 is, for example, a network interface card (NIC), and performs communication with other devices.

The memory 134 is, for example, a hard disk or a semiconductor memory device, and stores various types of information. Specifically, the memory 134 according to the first embodiment stores the volume data obtained from the image storage device 120 via the communication unit 133. The memory 134 according to the first embodiment also stores, for example, the volume data while being processed by the rendering processing and the stereoscopic image after being processed by the rendering processing.

The controller 135 includes an electronic circuit such as a central processing unit (CPU) or a micro processing unit (MPU), and an integrated circuit such as an application specific integrated circuit (ASIC) or a field programmable gate array (FPGA), and performs overall control of the workstation 130.

For example, the controller 135 according to the first embodiment controls the display of the GUIs and the display of the parallax image group for the display unit 132. The controller 135 also controls, for example, sending and receiving of the volume data and the parallax image group to and from the image storage device 120 via the communication unit 133. The controller 135 further controls, for example, the rendering processing performed by the rendering processor 136. The controller 135 still further controls, for example, reading of the volume data from the memory 134, and storing of the parallax image group into the memory 134.

Under the control of the controller 135, the rendering processor 136 applies various types of rendering processing to the volume data obtained from the image storage device 120, and generates a parallax image group. Specifically, the rendering processor 136 according to the first embodiment reads the volume data from the memory 134, and, first of all, preprocesses the volume data. Next, the rendering processor 136 applies the volume rendering processing to the preprocessed volume data, and generates the parallax image group. Subsequently, the rendering processor 136 generates a two-dimensional image in which various types of information (such as scale marks, a patient name, and inspection items) are represented, and superimposes the generated two-dimensional image on each image in the parallax image group to generate two-dimensional images for output. Then, the rendering processor 136 stores the parallax image group and the two-dimensional images for output thus generated in the memory 134. In the first embodiment, the rendering processing refers to the entire image processing applied to the volume data, and the volume rendering processing refers to the processing for generating the two-dimensional images (volume rendering image) reflecting three-dimensional information, in the rendering processing.

Figure 5:
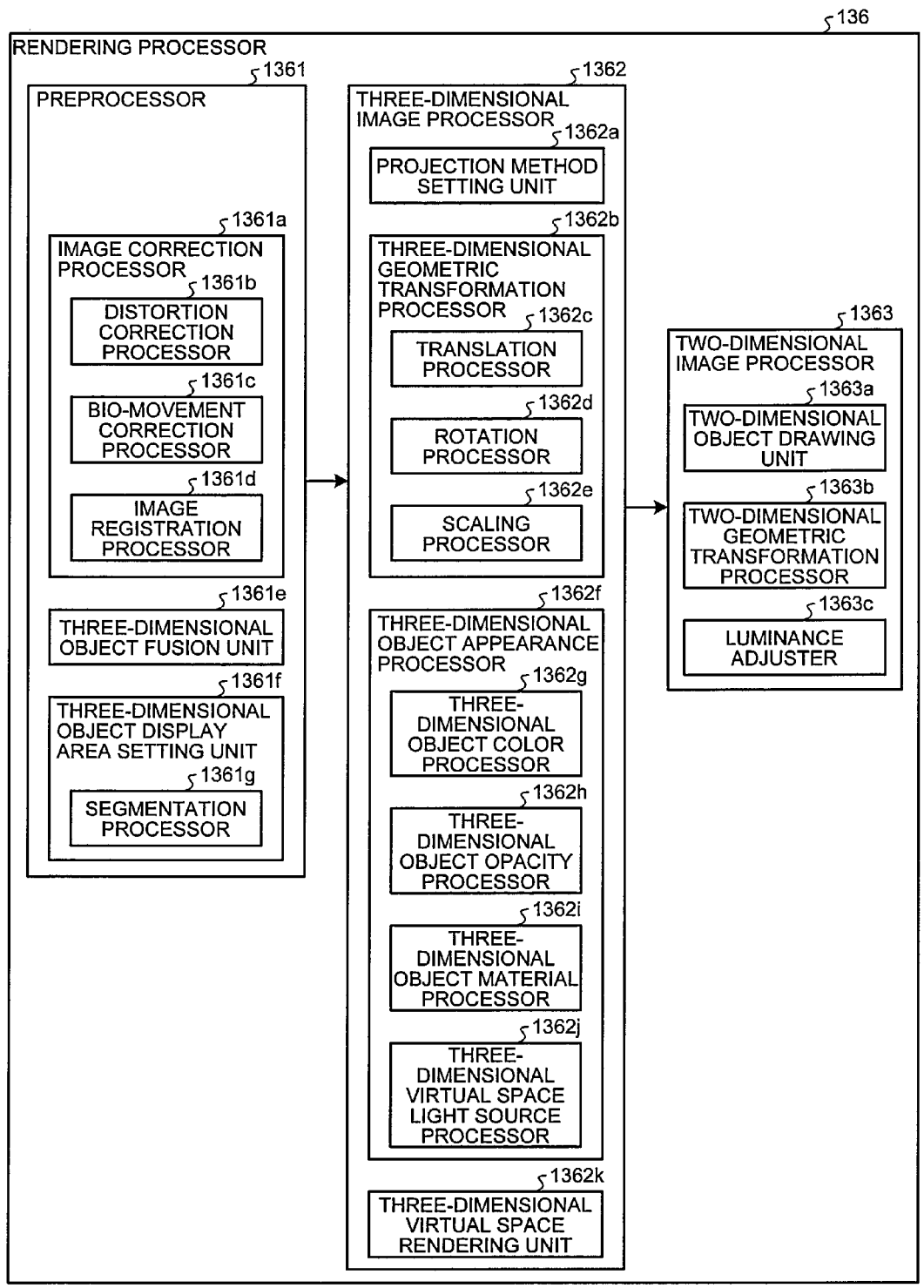
FIG. 5 is a diagram for explaining a configuration example of a rendering processor illustrated in FIG. 4.

FIG. 5 is a diagram for explaining a configuration example of the rendering processor illustrated in FIG. 4. As illustrated in FIG. 5, the rendering processor 136 includes a preprocessor 1361, a three-dimensional image processor 1362, and a two-dimensional image processor 1363. The preprocessor 1361 preprocesses the volume data. The three-dimensional image processor 1362 generates a parallax image group from the preprocessed volume data. The two-dimensional image processor 1363 generates the two-dimensional images for output which is the stereoscopic image with the various types of information superimposed thereon. The processors will be described below in sequence.

The preprocessor 1361 is a processor that applies various types of preprocessing to the volume data before being subjected to the rendering processing, and includes an image correction processor 1361a, a three-dimensional object fusion unit 1361e, and a three-dimensional object display area setting unit 1361f.

The image correction processor 1361a is a processor that performs image correction processing when two types of volume data are processed as one piece of volume data, and, as illustrated in FIG. 5, includes a distortion correction processor 1361b, a bio-movement correction processor 1361c, and an image registration processor 1361d. For example, the image correction processor 1361a performs the image correction processing when volume data of a PET image and volume data of an X-ray CT image that have been generated by the PET-CT apparatus are processed as one piece of volume data. Alternatively, the image correction processor 1361a performs the image correction processing when volume data of a T1-weighted image and volume data of a T2-weighted image that have been generated by the MRI apparatus are processed as one piece of volume data.

The distortion correction processor 1361b corrects distortion of data in each individual piece of the volume data caused by collection conditions at the time of data collection by the medical diagnostic imaging apparatus 110. The bio-movement correction processor 1361c corrects a movement caused by a subject's body movement occurring at the time when pieces of data used for generating the individual piece of volume data are collected. The image registration processor 1361d performs position alignment (registration) between two pieces of volume data that have been subjected to the correction processes by the distortion correction processor 1361b and the bio-movement correction processor 1361c, for example, by using a cross-correlation method.

The three-dimensional object fusion unit 1361e fuses a plurality of pieces of volume data whose positions are aligned by the image registration processor 1361d. Note that the processes of the image correction processor 1361a and the three-dimensional object fusion unit 1361e are omitted when the rendering processing is applied to a single piece of volume data.

The three-dimensional object display area setting unit 1361f is a processor that sets a display area corresponding to an organ to be displayed specified by the operator, and includes a segmentation processor 1361g. The segmentation processor 1361g is a processor that extracts an organ, such as a heart, a lung, or a blood vessel, specified by the operator, for example, by using a region growing method based on pixel values (voxel values) of the volume data.

The segmentation processor 1361g does not perform the segmentation processing if the operator has not specified any organ to be displayed. If the operator has specified a plurality of organs to be displayed, the segmentation processor 1361g extracts the specified organs. The processing of the segmentation processor 1361g may be executed again following a request for fine adjustment by the operator who has referred to the rendering image.

The three-dimensional image processor 1362 applies the volume rendering processing to the volume data preprocessed by the preprocessor 1361. As a processor performing the volume rendering processing, the three-dimensional image processor 1362 includes a projection method setting unit 1362*a*, a three-dimensional geometric transformation processor 1362*b*, a three-dimensional object appearance processor 1362*f*, and a three-dimensional virtual space rendering unit 1362*k*.

The projection method setting unit 1362*a* determines a projection method for generating the parallax image group. For example, the projection method setting unit 1362*a* determines whether the volume rendering processing is to be executed by a parallel projection method or a perspective projection method.

The three-dimensional geometric transformation processor 1362*b* is a processor that determines information for three-dimensional geometric transformation of the volume data to be subjected to the volume rendering processing, and includes a translation processor 1362*c*, a rotation processor 1362*d*, and a scaling processor 1362*e*. The translation processor 1362*c* is a processor that determines an amount of movement by which the volume data is to be translated if a viewpoint position when the volume rendering processing is performed is translated. The rotation processor 1362*d* is a processor that determines an amount of movement by which the volume data is to be rotationally moved if a viewpoint position when the volume rendering processing is performed is rotationally moved. The scaling processor 1362*e* is a processor that determines an enlargement ratio or a contraction ratio of the volume data when enlargement or contraction of the stereoscopic image is required.

The three-dimensional object appearance processor 1362*f* includes a three-dimensional object color processor 1362*g*, a three-dimensional object opacity processor 1362*h*, a three-dimensional object material processor 1362*i*, and a three-dimensional virtual space light source processor 1362*j*. The three-dimensional object appearance processor 1362*f* uses these processors to perform processing to determine the display state of a displayed stereoscopic image, for example, in response to a request from the operator.

The three-dimensional object color processor 1362*g* is a processor that determines a color in which each segmented area in the volume data is to be colored. The three-dimensional object opacity processor 1362*h* is a processor that determines opacity of voxels constituting each segmented area in the volume data. Note that, in the volume data, an area behind the area in which the opacity is set to 100% is not represented in the stereoscopic image. Note also that, in the volume data, an area in which the opacity is set to 0% is not represented in the stereoscopic image.

The three-dimensional object material processor 1362*i* is a processor that determines material of each segmented area in the volume data so as to adjust texture of the area when represented. The three-dimensional virtual space light source processor 1362*j* is a processor that determines position and type of a virtual light source placed in a three-dimensional virtual space when the volume rendering processing is applied to the volume data. The type of the virtual light source includes, for example, a light source that emits parallel light beams from an infinite distance and a light source that emits radial light beams from a viewpoint.

The three-dimensional virtual space rendering unit 1362*k* applies the volume rendering processing to the volume data, and generates a parallax image group. When applying the volume rendering processing, the three-dimensional virtual space rendering unit 1362*k* uses, as necessary, various types of information determined by the projection method setting unit 1362*a*, the three-dimensional geometric transformation processor 1362*b*, and the three-dimensional object appearance processor 1362*f*.

Here, the three-dimensional virtual space rendering unit 1362*k* applies the volume rendering processing in accordance with the rendering conditions. A rendering condition is, for example, "parallel projection method" or "perspective projection method". Another rendering condition is, for example, "standard viewpoint position and parallax angle". Further another rendering condition is, for example, "translation of viewpoint position", "rotational movement of viewpoint position", "enlargement of stereoscopic image, or "contraction of stereoscopic image". Still another rendering condition is, for example, "color used for coloring", "transparency(opacity)", "texture", "position of virtual light source", or "type of virtual light source". The rendering conditions such as mentioned above can be accepted from the operator via the input unit 131 or can be initialized. In either case, the three-dimensional virtual space rendering unit 1362*k* accepts the rendering conditions from the controller 135, and applies the volume rendering processing to the volume data in accordance with the accepted rendering conditions. When the volume rendering processing is applied, the projection method setting unit 1362*a*, the three-dimensional geometric transformation processor 1362*b*, and the three-dimensional object appearance processor 1362*f* determine various types of necessary information in accordance with the rendering conditions. Accordingly, the three-dimensional virtual space rendering unit 1362*k* uses the various types of information thus determined to generate the parallax image group.

Figure 6A:
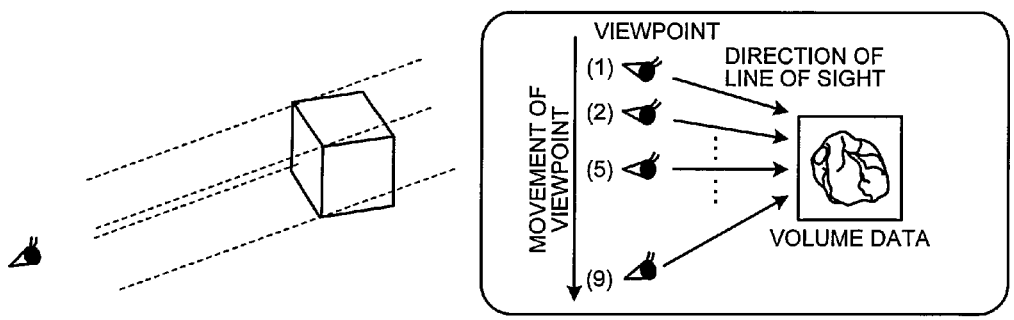
FIG. 6A, FIG. 6B, and FIG. 6C are diagrams for explaining an example of volume rendering processing according to the first embodiment.
Figure 6B:
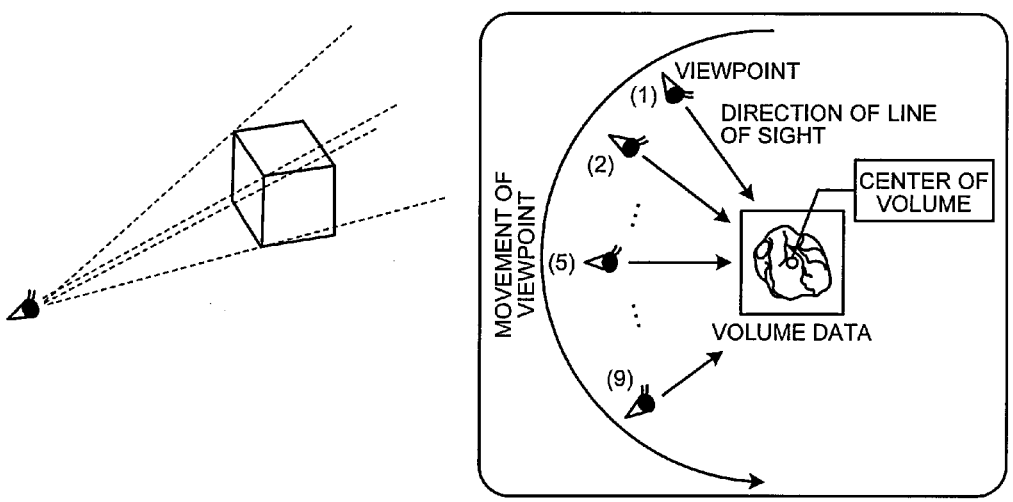
Figure 6C:
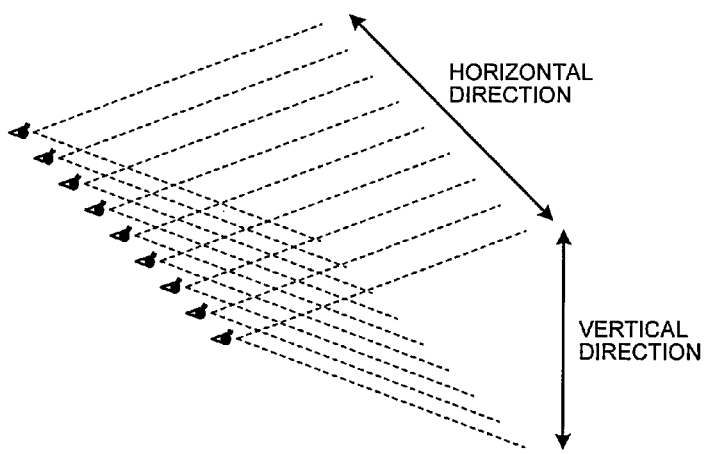

Each of FIGS. 6A, 6B, and 6C is a diagram for explaining an example of the volume rendering processing according to the first embodiment. For example, it is assumed that, as illustrated in FIG. 6A, the three-dimensional virtual space rendering unit 1362*k* accepts the parallel projection method, and further accepts a standard viewpoint position (5) and a parallax angle of one degree as rendering conditions. In such a case, the three-dimensional virtual space rendering unit 1362*k* sets a light source that emits parallel light beams from an infinite distance along a line of sight, as illustrated in FIG. 6A. Then, the three-dimensional virtual space rendering unit 1362*k* translates the position of the viewpoint from (1) to (9) so that the parallax angle is changed at intervals of one degree, and thus, generates nine parallax images having parallax angles changed at the intervals of one degree by using the parallel projection method.

Alternatively, it is assumed that as illustrated in FIG. 6B, the three-dimensional virtual space rendering unit 1362*k* accepts the perspective projection method, and further accepts the standard viewpoint position (5) and the parallax angle of one degree as rendering conditions. In such a case, the three-dimensional virtual space rendering unit 1362*k* sets, at each viewpoint, a point light source or a surface light source that radially emits light in a three-dimensional manner along lines of sight coming from a center, as illustrated in FIG. 6B. Then, the three-dimensional virtual space rendering unit 1362*k* rotationally moves the position of the viewpoint from (1) to (9), for example, so that the parallax angle is changed at intervals of one degree about the center (centroid) of a sectional plane of the volume data, and thus, generates nine parallax images having parallax angles changed at the intervals of one degree by using the perspective projection method. The perspective projection method may be used in the case in which the viewpoints (1) to (9) are translated, depending on the rendering conditions. The lines of sight are directed from the viewpoints to the center (centroid) of the sectional plane of the volume data as illustrated in FIGS. 6A and 6B.

Further alternatively, the three-dimensional virtual space rendering unit 1362k may perform the volume rendering processing using a combination of the parallel projection method and the perspective projection method by setting a light source that radially emits light in a two-dimensional manner along lines of sight coming from a center with respect to the vertical direction of the displayed volume rendering image, and that emits parallel light beams from an infinite distance along a line of sight with respect to the horizontal direction of the displayed volume rendering image, as illustrated in FIG. 6C.

The nine parallax images generated in this manner serve as the stereoscopic image. In the first embodiment, the nine parallax images are, for example, converted by the controller 135 into the intermediate image in which the nine images are arranged in the predetermined format (such as a grid pattern), and then, output to the display unit 132 serving as a nine-parallax monitor. Then, the operator of the workstation 130 can perform operations for generating the stereoscopic image while checking the stereoscopically viewable medical image displayed on the stereoscopic display monitor.

In the examples of FIGS. 6A, 6B, and 6C, the cases have been described in which the projection method and the standard viewpoint position and parallax angle are accepted as rendering conditions. However, even in the case in which other conditions are accepted as rendering conditions, the three-dimensional virtual space rendering unit 1362k generates the parallax image group in the same manner while reflecting each of the rendering conditions.

The three-dimensional virtual space rendering unit 1362k also has, in addition to the volume rendering function, a function to reconstruct an MPR image from the volume data by using a multiplanar reconstruction (MPR) method. The three-dimensional virtual space rendering unit 1362k also has a function to perform curved MPR and a function to perform intensity projection.

Subsequently, the parallax image group generated from the volume data by the three-dimensional image processor 1362 is used as underlays. Then, the overlay in which the various types of information (such as scale marks, a patient name, and inspection items) are represented is superimposed on the underlays so as to form the two-dimensional images for output. The two-dimensional image processor 1363 is a processor that generates the two-dimensional images for output by applying image processing to the overlay and the underlays, and, as illustrated in FIG. 3, includes a two-dimensional object drawing unit 1363a, a two-dimensional geometric transformation processor 1363b, and a luminance adjuster 1363c. For example, in order to reduce the load required for the generation processing of the two-dimensional images for output, the two-dimensional image processor 1363 makes nine respective parallax images (underlays) superimposed by one overlay to generate nine two-dimensional images for output.

The two-dimensional object drawing unit 1363a is a processor that draws the various types of information to be represented on the overlay. The two-dimensional geometric transformation processor 1363b is a processor that translates or rotationally moves positions of the various types of information to be represented on the overlay and that enlarges or contracts the various types of information to be represented on the overlay.

The luminance adjuster 1363c is a processor that performs luminance conversion processing, and is a processor that adjusts luminance levels of the overlay and the underlays depending on parameters for image processing, such as the gradation, the window width (WW), and the window level (WL) of the monitor that receives the output.

The two-dimensional images for output generated by the rendering processor 136 are, for example, once stored in the memory 134 by the controller 135. The two-dimensional images for output generated by the rendering processor 136 according to the present embodiment form a two-dimensional image group for stereoscopic viewing having the parallax images as the underlays, and such as two-dimensional image group serves as the parallax image group.

The two-dimensional image group for output (parallax image group) is, for example, sent by the controller 135 to the image storage device 120 via the communication unit 133 as illustrated in FIG. 4.

The controller 135 performs control, for example, so that the parallax image group generated by the rendering processor 136 is stored in a corresponding manner to the volume data which is a generation source of the parallax image group.

Figure 7:
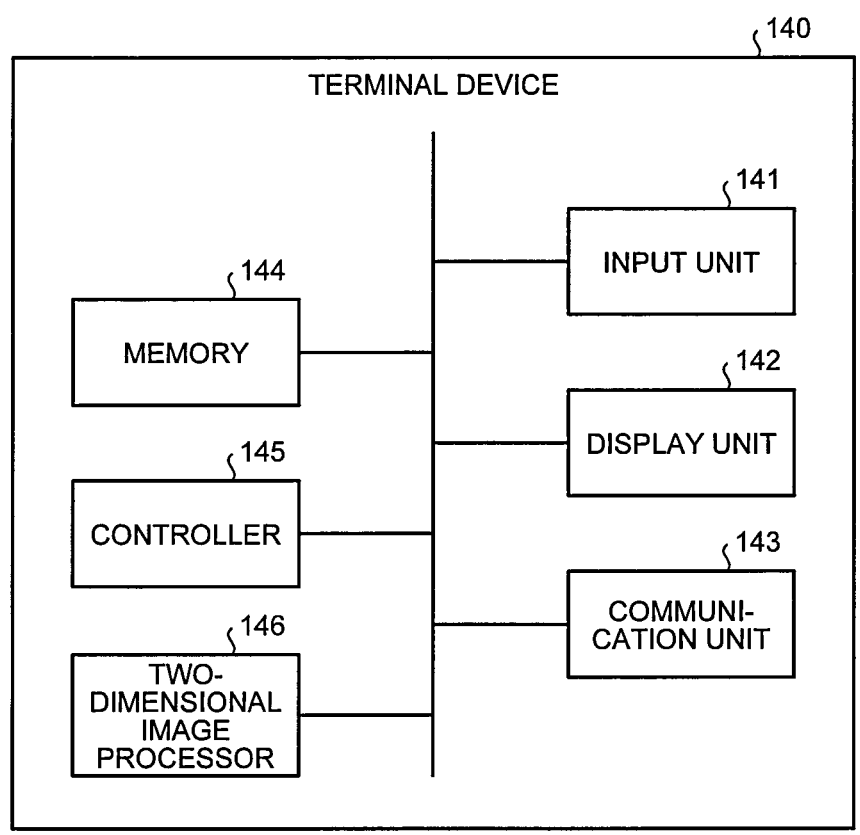
FIG. 7 is a diagram for explaining a configuration example of a terminal device according to the first embodiment.

The terminal device 140 according to the first embodiment is, as described above, a device for allowing the medical doctors and the inspection engineers working in the hospital to view the medical images, and obtains, from the image storage device 120, the parallax image group (two-dimensional images for output) generated by the rendering processor 136. FIG. 7 is a diagram for explaining a configuration example of the terminal device according to the first embodiment.

As illustrated in FIG. 7, the terminal device 140 according to the first embodiment includes an input unit 141, a display unit 142, a communication unit 143, a memory 144, a controller 145, and a two-dimensional image processor 146.

The input unit 141 includes, for example, a mouse, a keyboard, and a trackball, and accepts input of various operations for the terminal device 140 from the operator. Specifically, the input unit 141 according to the first embodiment accepts a stereoscopic vision request from the operator. For example, the input unit 141 accepts, as the stereoscopic vision request, input of information, such as the patient ID, the inspection ID, the apparatus ID, and the series ID, used by the operator for specifying the volume data requested to be stereoscopically viewed.

The display unit 142 is, for example, a liquid crystal panel serving as the stereoscopic display monitor, and displays various types of information. Specifically, the display unit 142 according to the first embodiment displays graphical user interfaces (GUIs) for accepting various operations from the operator and stereoscopic images. For example, the display unit 142 is the stereoscopic display monitor described using FIG. 2 (hereinafter mentioned as two-parallax monitor), or a stereoscopic display monitor described using FIG. 5 (hereinafter mentioned as nine-parallax monitor). Description will be made below of the case in which the display unit 142 is the nine-parallax monitor.

The communication unit 143 is, for example, a network interface card (NIC), and performs communication with other devices. Specifically, the communication unit 143 according to the first embodiment sends the stereoscopic vision request accepted by the input unit 141 to the image storage device 120. The communication unit 143 according to the first embodiment also receives the parallax image group sent by the image storage device 120 in response to the stereoscopic vision request.

The memory 144 is, for example, a hard disk or a semiconductor memory device, and stores various types of information. Specifically, the memory 144 according to the first embodiment stores the parallax image group obtained from the image storage device 120 via the communication unit 143. The memory 144 also stores the supplementary information (such as the parallax number and the resolution) on the parallax image group received from the image storage device 120 via the communication unit 143.

The controller 145 includes an electronic circuit such as a central processing unit (CPU) or a micro processing unit (MPU), and an integrated circuit such as an application specific integrated circuit (ASIC) or a field programmable gate array (FPGA), and performs overall control of the terminal device 140.

For example, the controller 145 controls sending and receiving of the stereoscopic vision request and the parallax image group to and from the image storage device 120 via the communication unit 143. The controller 145 also controls, for example, storing and reading of the parallax image group into and from the memory 144.

The controller 145 according to the first embodiment also controls the display of the GUIs and the display of the parallax image group for the display unit 142. The controller 145 according to the first embodiment converts the stereoscopic image into an intermediate image in which the parallax images are arranged in a predetermined format (such as a grid pattern), and then, displays the stereoscopic image on the display unit 142 serving as the nine-parallax monitor.

The controller 145 according to the first embodiment also controls image processing performed by the two-dimensional image processor 146.

The two-dimensional image processor 146 has the same function as that of the two-dimensional image processor 1363 described using FIG. 5. More specifically, the two-dimensional image processor 146 can generate the two-dimensional images for output to the display unit 142 by generating an overlay and superimposing it on the parallax image group serving as underlays generated by the three-dimensional image processor 1362.

The two-dimensional image processor 146 according to the first embodiment further has an interpolation function that performs interpolation processing to generate a new parallax image from two parallax images by using respective depth information of the two parallax images. The interpolation function of the two-dimensional image processor 146 will be described later in detail.

As described above, the rendering processor 136 generates the parallax image group under the control of the controller 135. The terminal device 140 obtains the parallax image group from the image storage device 120, and displays the obtained parallax image group on the display unit 142. As a result, the medical doctor or the inspection engineer acting as the operator of the terminal device 140 can view the stereoscopically viewable medical image in the state in which the various types of information (such as scale marks, a patient name, and inspection items) are represented.

However, in order for the rendering processor 136 to generate in real-time the parallax image group by performing the volume rendering processing in response to the stereoscopic vision request from the terminal device 140, the workstation 130 is required to have a high image processing capacity.

Accordingly, in the workstation 130 according to the first embodiment, the controller 135 performs rendering processing control so as to reduce the load of processing required for generating the image for stereoscopic viewing from the three-dimensional medical image data. More specifically, under the control of the controller 135, the workstation 130 generates, from the volume data, an image group (parallax image group) including as many images as or more images than the parallax number required by the rendering processor 136 for achieving a stereoscopic view on a predetermined monitor. Then, in the workstation 130 according to the first embodiment, the controller 135 performs control so as to store the parallax image group generated by the rendering processor 136 in the image storage device 120. Then, a stereoscopic monitor (such as the display unit 142) displays a stereoscopic image (such as a nine-parallax image) constituted by selecting as many parallax images as the parallax number out of the parallax image group stored in the image storage device 120.

For example, the operator of the workstation 130 according to the first embodiment obtains the maximum value of the parallax number from the information on the numbers of parallaxes required by respective stereoscopic monitors included in devices connected to the in-hospital LAN 2. Then, the operator sets predetermined rendering conditions including the parallax number for the controller 135 so as to generate a parallax image group constituted by parallax images totaling as many as or more than the obtained maximum value. Description will be made below of the case in which the maximum value is 9, which is the parallax number of the display unit 142 of the terminal device 140. Note that the present embodiment can also be applied to the case in which the maximum value is, for example, 18 or 2.

Then, the controller 135 controls the rendering processing of the rendering processor 136 based on the information on the parallax number and on the preset rendering conditions. More specifically, the controller 135 controls the rendering processor 136 to generate the parallax image group, by setting, based on straight or curved lines to form a figure having a predetermined shape, viewpoints for performing the rendering processing as many as or more than the parallax number. Description will be made below of various rendering conditions that are set in the first embodiment.

The above-mentioned figure having the predetermined shape that is set as a rendering condition of the present embodiment is broadly classified into the following two types depending on the positional relationship between viewpoints and a rendering area serving as an area to be rendered in the volume data. That is, under a first figure condition, the controller 135 sets the figure having the predetermined shape so that the viewpoints are located outside the rendering area. Then, the controller 135 controls the rendering processor 136 to generate the parallax image group by using straight or curved lines that form the figure thus set. On the other hand, under a second figure condition, the controller 135 sets, as the figure having the predetermined shape, a figure where the viewpoints are located in the rendering area. Then, the controller 135 controls the rendering processor 136 to generate the parallax image group by using straight or curved lines that form the figure thus set.

A rendering condition of the present embodiment is broadly classified into the following two types depending on the number of parallax images constituting the parallax image group. That is, under a first image count condition, the controller 135 controls to generate the parallax image group constituted by as many parallax images as the parallax number required for being stereoscopically viewed. On the other hand, under a second image count condition, the controller 135 controls to generate the parallax image group constituted by more parallax images than the parallax number required for being stereoscopically viewed.

When the first figure condition is set as a rendering condition of the present embodiment, the first figure condition is further classified into the following two types depending on a viewpoint setting method. That is, under a first viewpoint setting condition, the controller 135 sets the viewpoints for performing the rendering processing as many as or more than the parallax number along the straight or curved lines that form the figure having the predetermined shape. On the other hand, under a second viewpoint setting condition, the controller 135 sets the viewpoints for performing the rendering processing as many as or more than the parallax number along a tangent line at a point set on the straight or curved lines that form the figure having the predetermined shape.

The rendering conditions include, for example, the parallax angle, the projection method, and the segmentation condition as described above. Description will be made below of the case in which the parallax angle is set to one degree. However, the parallax angle can be set to any value. For example, the parallax angle can be 0.5 degree, 0.1 degree, or 3 degrees.

Figure 8A:
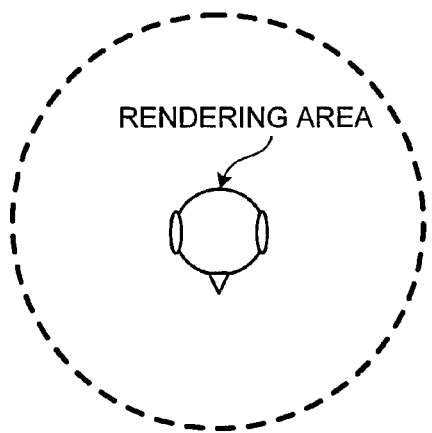
FIG. 8A, FIG. 8B, and FIG. 8C are diagrams for explaining rendering processing performed under a first figure condition and a first image count condition.
Figure 8B:
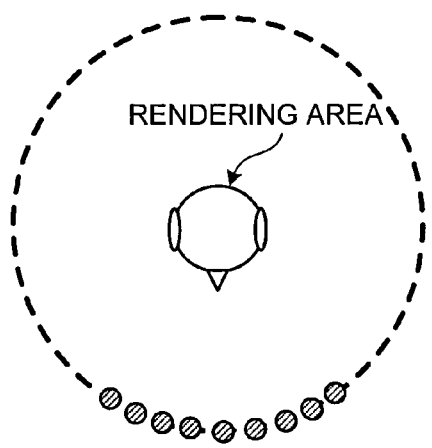
Figure 8C:
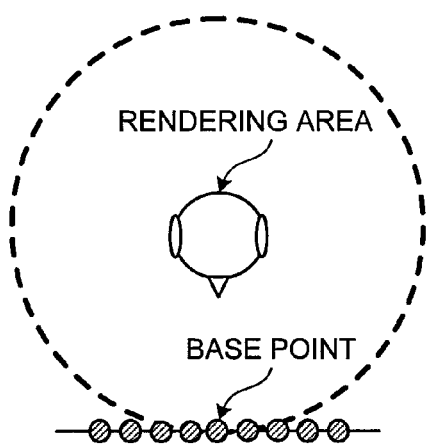

First, description will be made of the rendering processing performed under the first figure condition and the first image count condition. FIGS. 8A, 8B, and 8C are diagrams for explaining the rendering processing performed under the first figure condition and the first image count condition. For example, as illustrated in FIG. 8A, the controller 135 sets a perfect circle as a figure where the viewpoints are located outside the rendering area under the first figure condition.

For example, the controller 135 obtains the position of the centroid of a rendering area extracted by the segmentation processor 1361g. Then, the controller 135 set a perfect circle intersecting perpendicularly with a rotation axis passing through the centroid. In this case, the controller 135 sets the radius of the perfect circle so that the outer circumference of the perfect circle is located outside of the rendering area. There may be a case in which the radius of the perfect circle is determined by the controller 135 based on the three-dimensional space coordinates of the rendering area, or by the operator of the workstation 130. In addition, the center of the perfect circle is not limited to the centroid of the rendering area, but may be set to an arbitrary position by the operator of the workstation 130, depending on a case. For example, there may be a case in which the center of the perfect circle is set to a place to be noted, such as an affected part. In such a case, the operator of the workstation 130 sets the place to be noted in the affected part as the center of the perfect circle, for example, by referring to an MPR image obtained by cutting the volume data along an arbitrary sectional plane. Alternatively, there may be a case in which the center of the perfect circle is set by detecting the place to be noted in the affected part by the workstation 130, for example, using an apparatus equipped with a computer assisted diagnosis (CAD) system which automatically detects a candidate region in a lesion.

Then, under the control of the controller 135, the rendering processor 136 generates the nine-parallax image having the parallax angle of one degree.

For example, if the first viewpoint setting condition is set, the controller 135 sets nine viewpoints along the circumference of the perfect circle so that the parallax angle is one degree, as illustrated in FIG. 8B. Then, if the first viewpoint setting condition is set, the rendering processor 136 generates, using the nine viewpoints thus set, the nine-parallax image by using the perspective projection method described in FIG. 6B. The positions of the nine viewpoints are set by the operator or the controller 135. Note that the direction of line of sight at each of the nine viewpoints needs to meet conditions allowing stereoscopic vision display. The direction of line of sight at each of the nine viewpoints is set, for example, to be a direction toward the center (centroid) in the sectional plane of the volume data, as illustrated in FIGS. 6A and 6B.

On the other hand, if the second viewpoint setting condition is set, the controller 135 sets a base point on the perfect circle, and sets nine viewpoints along a tangent line passing through the base point so that the parallax angle is one degree, as illustrated in FIG. 8C. Then, if the second viewpoint setting condition is set, the rendering processor 136 generates, using the nine viewpoints thus set, the nine-parallax image by using the parallel projection method described in FIG. 6A. Note that, if the second viewpoint setting condition is set, the rendering processor 136 may use the projection method described in FIG. 6C to generate the nine-parallax image. The position of the base point is set by the operator or the controller 135.

Figure 9A:
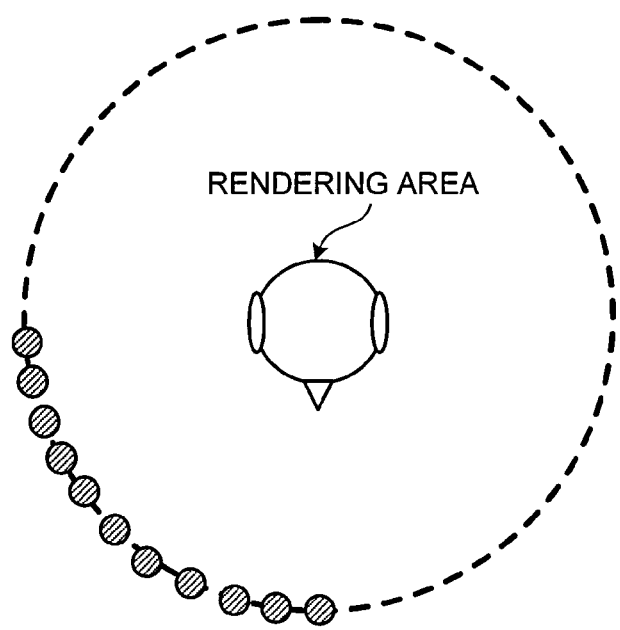
FIG. 9A, FIG. 9B, and FIG. 10 are diagrams for explaining the rendering processing performed under the first figure condition and a second image count condition.
Figure 9B:
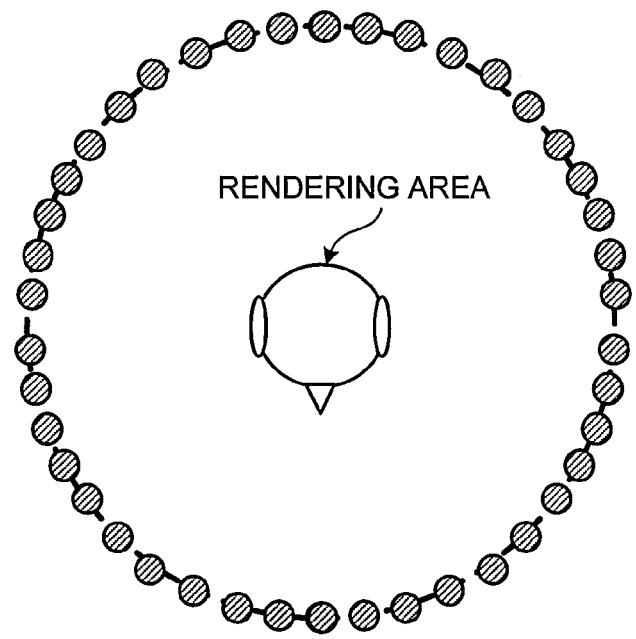
Figure 10:
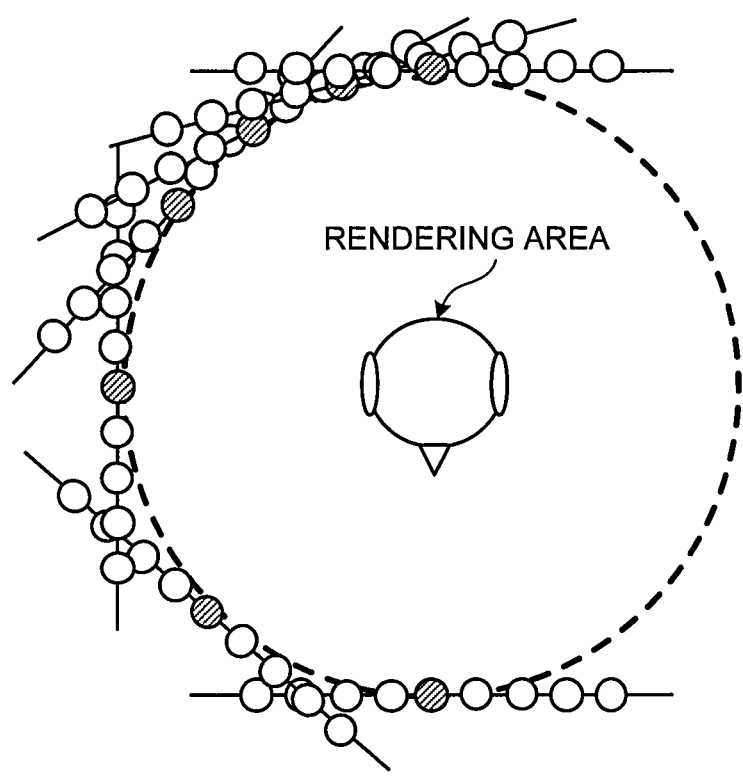

Next, description will be made of the rendering processing performed under the first figure condition and the second image count condition. FIGS. 9A, 9B, and 10 are diagrams for explaining the rendering processing performed under the first figure condition and the second image count condition. First, for example, as has been described in FIG. 8A, the controller 135 sets a perfect circle as a figure where the viewpoints are located outside the rendering area under the first figure condition. The parallax number set by the second image count condition is 10 or more.

Here, if the parallax number is set to 11 by the second image count condition, and also the first viewpoint setting condition is set, the controller 135 sets 11 viewpoints along the circumference of the perfect circle so that the parallax angle is one degree, as illustrated in FIG. 9A. Then, the rendering processor 136 generates, using the 11 viewpoints thus set, a parallax image group constituted by 11 parallax images.

If the parallax number is set to 360 by the second image count condition, and also the first viewpoint setting condition is set, the controller 135 sets 360 viewpoints along the entire circumference of the perfect circle so that the parallax angle is one degree, as illustrated in FIG. 9B. Note that, although only 42 viewpoints are represented in FIG. 9B for convenience of drawing, 360 viewpoints are actually set. Then, the rendering processor 136 generates, using the 360 viewpoints thus set, a parallax image group constituted by 360 parallax images. Hereinafter, the parallax images generated on the entire circumference for the area to be rendered, as illustrated in FIG. 9B, are mentioned as entire circumferential data.

If the second image count condition and the second viewpoint setting condition are set, the controller 135 sets the viewpoints for performing the rendering processing along each of the tangent line directions at a plurality of points set on the straight or curved lines that form the figure having the predetermined shape. For example, if the second image count condition and the second viewpoint setting condition are set, the controller 135 sets a plurality of base points on the perfect circle (refer to hatched circles in FIG. 10), and sets nine viewpoints along each of the tangent lines passing through the base points thus set so that the parallax angle is one degree, as illustrated in FIG. 10. Then, the rendering processor 136 generates, using the nine viewpoints set on each of the tangent lines, the nine-parallax image for each of the base points by using the parallel projection method described in FIG. 6A. Note that the rendering processor 136 may use the projection method described in FIG. 6C to generate the nine-parallax image for each of the base points. The positions of the base points are set by the operator or the controller 135.

Figure 11A:
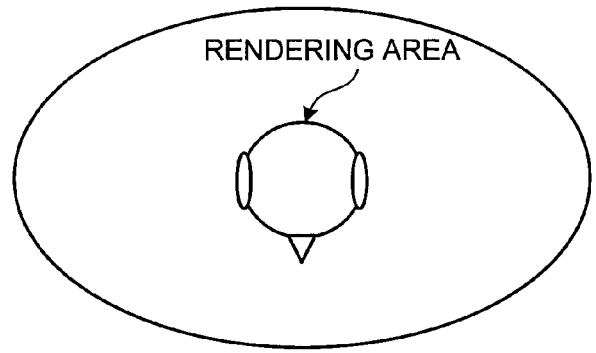
FIG. 11A, FIG. 11B, and FIG. 11C are diagrams for explaining a modification of the first figure condition.
Figure 11B:
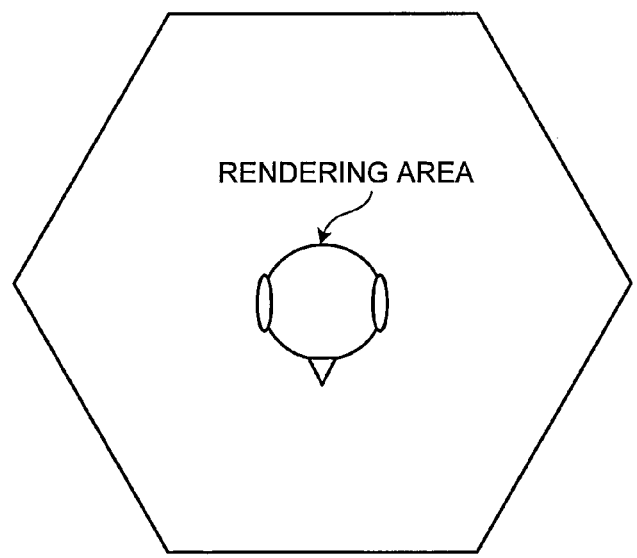
Figure 11C:
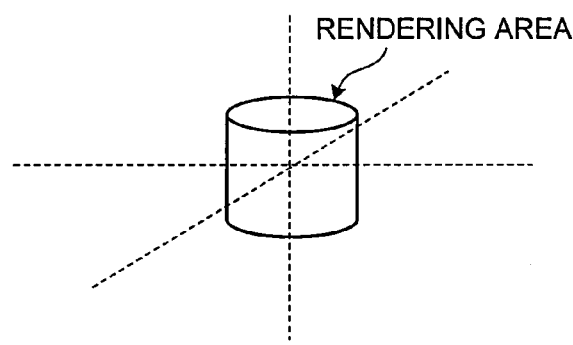

Note that the figure having the predetermined shape set by the first figure condition is not limited to a perfect circle. FIGS. 11A, 11B, and 11C are diagrams for explaining modifications of the first figure condition.

For example, there may be a case in which the figure having the predetermined shape set by the first figure condition is an ellipse as illustrated in FIG. 11A. The figure having the predetermined shape set by the first figure condition may be a polygon, and may be, for example, a hexagon as illustrated in FIG. 11B, depending on a case.

Moreover, the figure having the predetermined shape set by the first figure condition is not limited to the case of a closed figure composed of straight lines or curves. For example, there may be a case in which the figure having the predetermined shape set by the first figure condition is a polyline or a spline curve.

There may also be a case in which the controller 135 sets more than one of the figures each having the predetermined shape under the first figure condition. For example, as illustrated in FIG. 11C, the controller 135 may perform control so as to set three perfect circles by setting three axes of rotation passing through the centroid of the rendering area, and to generate a parallax image group in each of the perfect circles. By using a perfect circle as a figure where the viewpoints are located, the advantages described below are provided. In general, a rendering image at an arbitrary viewpoint is not necessarily a parallax image at that viewpoint. However, if, for example, the figure where the viewpoints are located is a perfect circle, the rendering image at an arbitrary viewpoint on the perfect circle is made to be a parallax image at that viewpoint by appropriately setting the condition of the parallax angle. That is, the number of images to be generated as a parallax image group can be significantly reduced by using a perfect circle as the figure where the viewpoints are located. As a result, the amount of data of the parallax image group to be stored can be significantly reduced.

In this manner, under the first figure condition, the controller 135 controls to generate the parallax image group by arbitrarily combining the first image count condition or the second image count condition with the first viewpoint setting condition or the second viewpoint setting condition.

Then, the controller 135 controls the image storage device 120 via the communication unit 133 to store the parallax image group generated by the rendering processor 136. Specifically, the controller 135 controls the image storage device 120 to store the parallax image group generated by the rendering processor 136 in a corresponding manner to the volume data which is a generation source of the parallax image group.

By such processing, the parallax image group is placed in a stored state, and, for example, the operator of the terminal device 140 can stereoscopically view the volume data on the display unit 142 by simply specifying the volume data to which the operator wants to refer.

Accordingly, the controller 145 of the terminal device 140 performs the following display control processing. That is, the controller 145 obtains, from the image storage device 120, the parallax image group of the volume data specified by the operator. Specifically, the controller 145 obtains, from the image storage device 120, as many parallax images as the parallax number out of the parallax image group generated from the volume data specified by the operator. For example, when the controller 145 accepts a stereoscopic vision request along with supplementary information, such as the patient ID and the inspection ID, from the operator of the terminal device 140 via the input unit 141, the controller 145 sends the supplementary information and the stereoscopic vision request to the image storage device 120. The image storage device 120 performs a search for volume data corresponding to the received supplementary information, and further performs a search for a parallax image group corresponding to the found volume data. Then, the image storage device 120 sends the found parallax image group to the terminal device 140.

Figure 12:
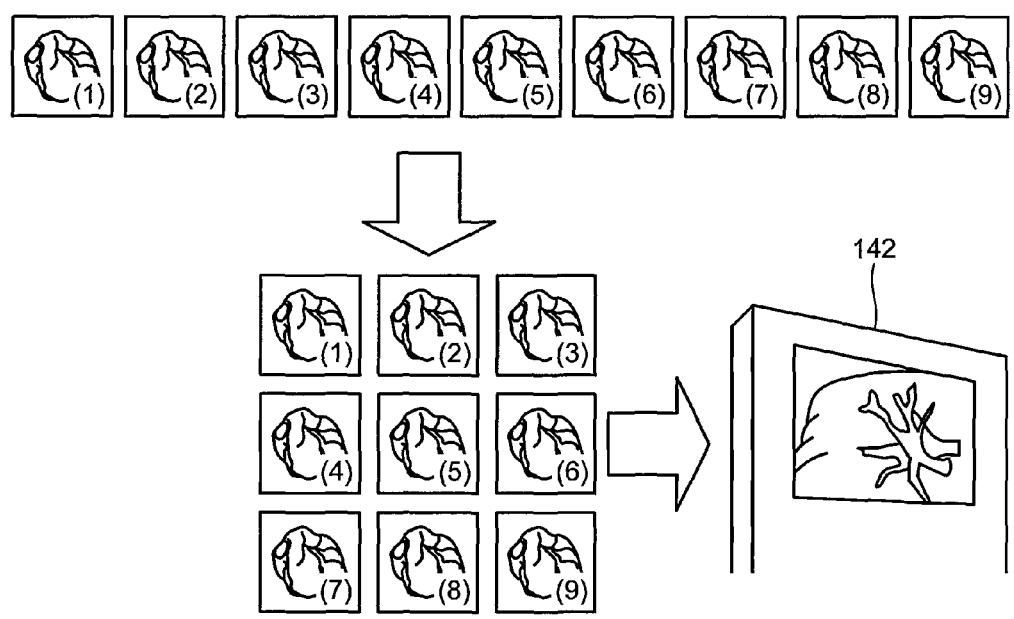
FIG. 12, FIG. 13, and FIG. 14 are diagrams for explaining display control in the terminal device.
Figure 13:
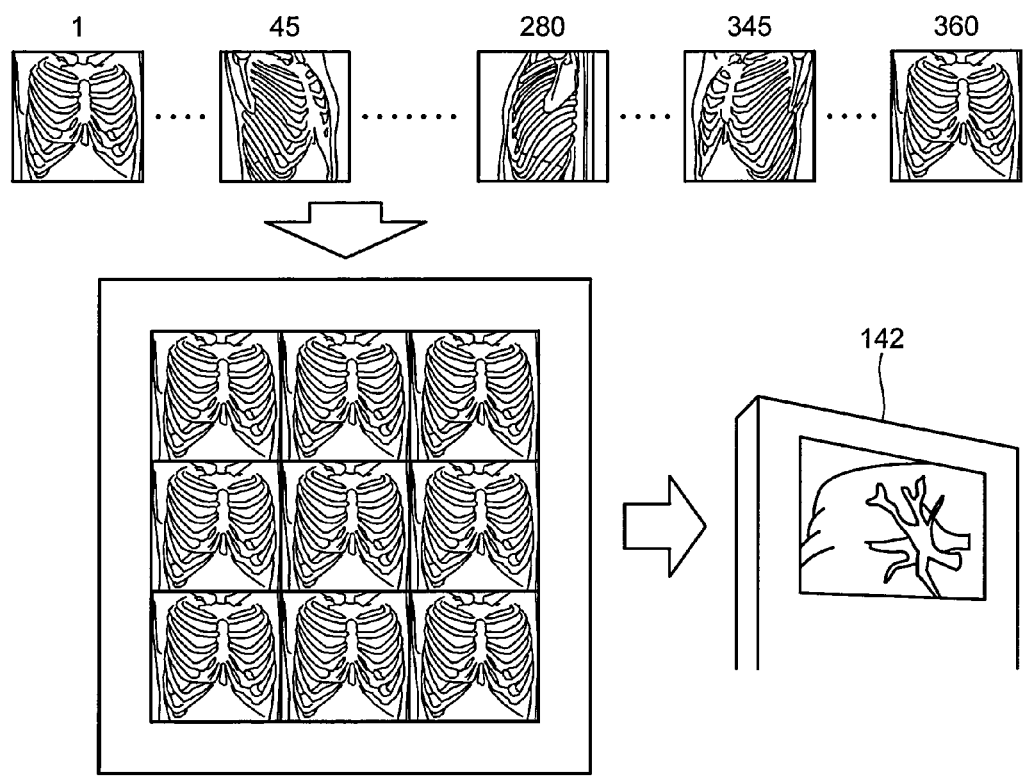
Figure 14:
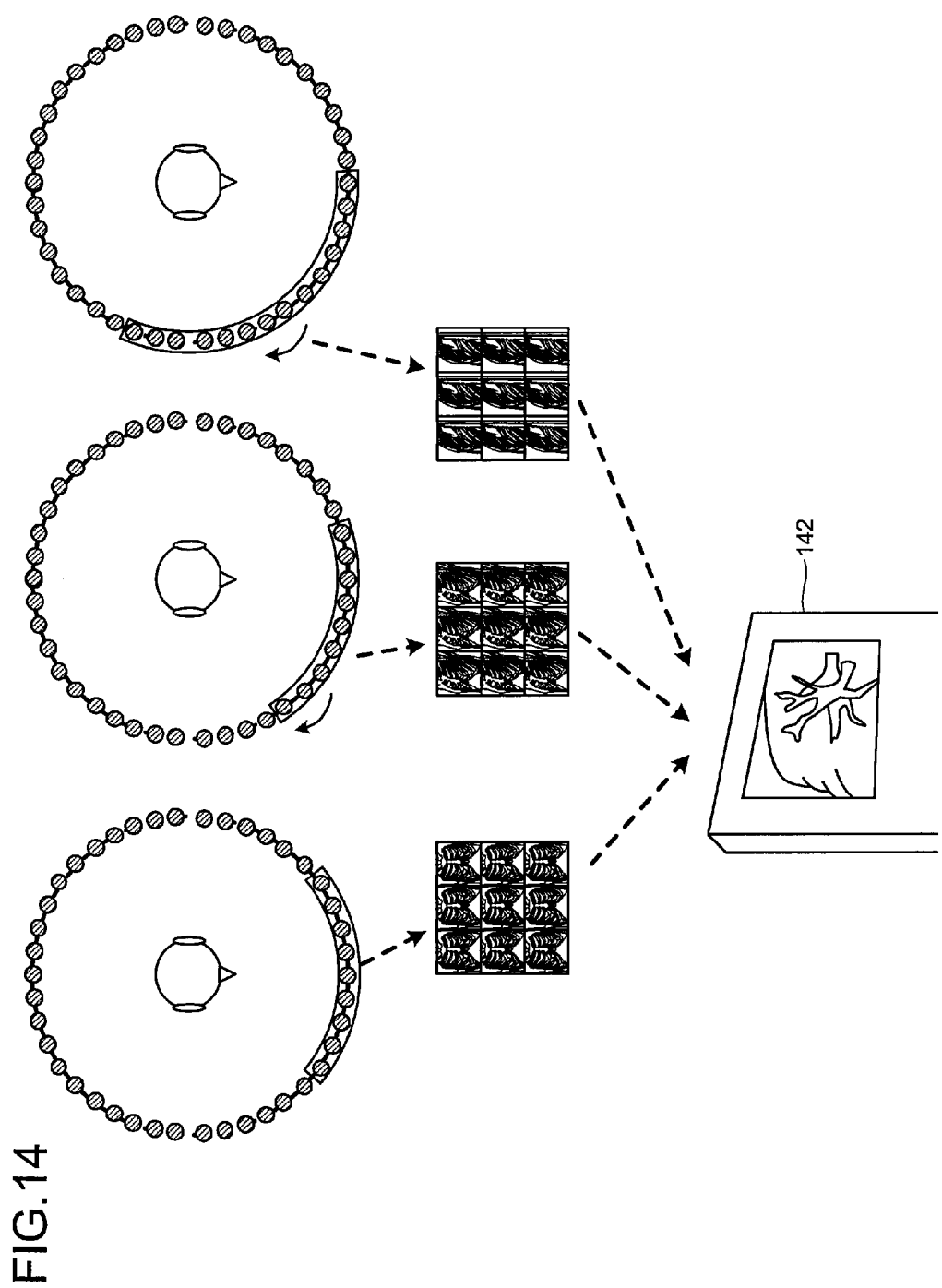

Then, the controller 145 performs control so as to display the stereoscopic image constituted by using as many obtained parallax images as the parallax number on the display unit 142 serving as a nine-parallax monitor. FIGS. 12 to 14 are diagrams for explaining the display control in the terminal device.

For example, when having obtained the parallax image group (nine-parallax image) generated by the first figure condition and the first image count condition described using FIG. 8, the controller 145 converts the nine-parallax image into an intermediate image in which the images are arranged in a grid pattern of three rows by three columns, and outputs the intermediate image to the display unit 142 to display the image thereon, as illustrated in FIG. 12. Note that the format of the intermediate image is not limited to a grid pattern. It is sufficient that the intermediate image has, for example, a format in which the two-parallax image is rearranged into a pixel arrangement corresponding to specifications of a nine-parallax monitor. Here, the specifications of a nine-parallax monitor include, for example, the vertical stripe liquid crystal display, the horizontal stripe liquid crystal display, the vertical lens type, the slanted lens type, and an angle of slanted lens.

On the other hand, when having obtained the parallax image group generated by the first figure condition and the second image count condition described using FIGS. 9 and 10, the controller 145 performs processing described below. More specifically, if the number of images in the parallax image group obtained from the image storage device 120 is larger than the parallax number, the controller 145 performs control so as to select a group of as many images as the parallax number from the obtained parallax image group and to display the selected group on the display unit 142.

For example, if the entire circumferential data is obtained, the controller 145 selects nine parallax images of successive viewpoint positions, then converts the images into a grid-like intermediate image, and outputs it to the display unit 142 to display the image thereon, as illustrated in FIG. 13. There may be a case in which the operator of the terminal device 140 selects the nine-parallax image. There may also be a case in which the workstation 130 selects the nine-parallax image in advance. The selection processing of nine-parallax image is not limited to the case of selecting the nine parallax images of successive viewpoint positions. For example, there may be a case in which the selection processing of nine-parallax image is performed by selecting every second successive viewpoint position or every third successive viewpoint position.

In the case in which the number of images in the parallax image group obtained from the image storage device 120 is larger than the parallax number, the controller 145 alternatively performs control so as to sequentially select groups of as many images as the parallax number from the obtained parallax image group and to sequentially display the selected groups on the display unit 142. Specifically, the controller 145 performs control so as to sequentially display more than one of the stereoscopic images on the display unit 142 by sequentially selecting as many parallax images as the parallax number.

For example, if the entire circumferential data is obtained, the controller 145 sequentially selects nine parallax images of successive viewpoint positions in a shifting manner in increments of several images, as illustrated in FIG. 14. Then, as illustrated in FIG. 14, the controller 145 sequentially converts the selected nine-parallax images into intermediate images, and sequentially outputs them to the display unit 142 to display the images thereon. As a result, the display unit 142 can display the stereoscopic image that the operator can stereoscopically observe while rotating the volume data. There may be a case in which the operator of the terminal device 140 selects the nine-parallax image. There may also be a case in which the workstation 130 selects the nine-parallax image in advance. It is not necessary for the number of images generated as the parallax image group by the rendering processor 136 to be equal to or more than the parallax number. Specifically, there may be a case in which parallax images totaling the parallax number or more are generated from parallax images totaling less than the parallax number generated by the rendering processor 136 by using the above-mentioned interpolation function of the two-dimensional image processor 146. For example, there may be a case in which the two-dimensional image processor 146 generates an image that can be used for a parallax image from two parallax images of adjacent viewpoint positions by using the interpolation processing, so as to generate parallax images totaling the parallax number or more. In other words, the present embodiment may be a case in which, by using the interpolation processing, the two-dimensional image processor 146 generates, under the control of the controller 145, parallax images totaling the parallax number or more from parallax images totaling less than the parallax number generated by the rendering processor 136 under the control of the controller 135. The interpolation function of the two-dimensional image processor 146 will be described later in detail.

Figure 15:
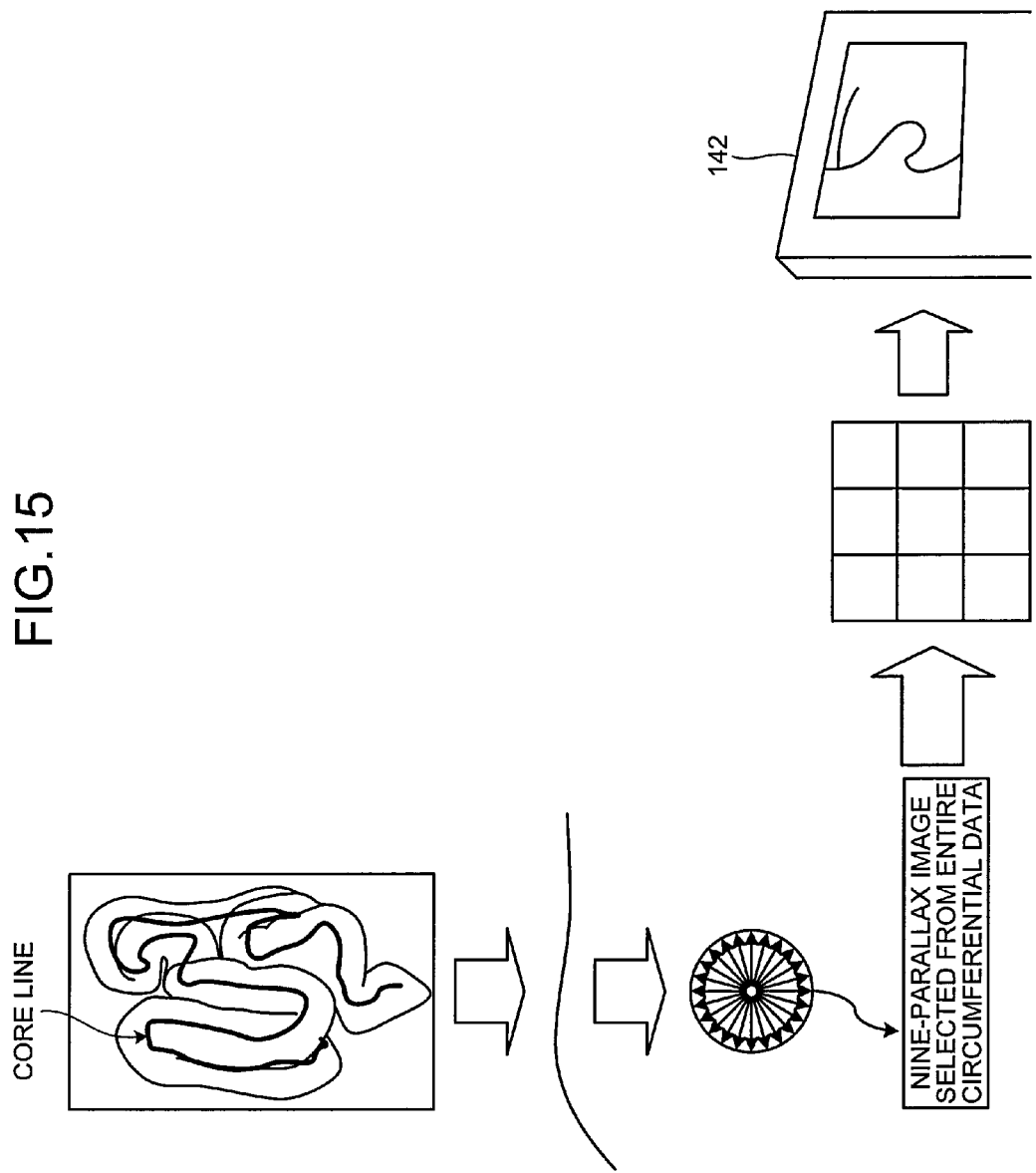
FIG. 15 is a diagram for explaining a second figure condition.

Next, the second figure condition will be described. Under the second figure condition, the controller 135 sets the figure having the predetermined shape so that the viewpoints are located in the rendering area. FIG. 15 is a diagram for explaining the second figure condition. The second figure condition is a condition applied to, for example, a case of performing a virtual endoscopy (VE) display method that is widely used as a display method (CT colonography [CTC]) for a three-dimensional X-ray CT image obtained by photographing a large intestine.

For example, the segmentation processor 1361g extracts a luminal area of a large intestine. The segmentation processor 1361g further extracts a core line of the luminal area as illustrated in FIG. 15. The core line extracted by the segmentation processor 1361g forms the figure having the predetermined shape used under the second figure condition. Then, as illustrated in FIG. 15, the segmentation processor 1361g further sets a plurality of base points at predetermined intervals on the extracted core line (refer to white circles in FIG. 15).

The controller 135 that has obtained such information sets viewpoints in the positions where the base points are located on the core line, and in a plane passing through each of the thus set viewpoints and perpendicular to the core line, sets a direction of line of sight for radially observing an inner wall of the large intestine (inner luminal wall) in one turn around the viewpoint, as illustrated in FIG. 15. By rotating the direction of line of sight by 360 degrees around each of the base points, the rendering processor 136 generates the entire circumferential data that allows the inner wall of the large intestine (inner luminal wall) to be stereoscopically viewed in one turn at each of the base points.

The thus generated parallax image groups of the VE display method are stored in the image storage device 120. The controller 145 then obtains the set of the image groups of the VE display method from the image storage device 120, and displays the set on the display unit 142. That is, the controller 145 converts the nine-parallax images selected from the entire circumferential data generated at the base points into intermediate images, and outputs them to the display unit 142. The first figure condition limits the positions of viewpoints to be outside the rendering area, and the second figure condition limits the positions of viewpoints to be inside the rendering area. However, the positions of viewpoints to be set in the first embodiment are not limited to those ranges. For example, the first embodiment may be a case in which the parallax image group used for the stereoscopic image is generated under a third figure condition, under which the figure is set so that some viewpoints are located in the rendering area while other viewpoints are located outside the rendering area. The figure set under the third figure condition may be any of a perfect circle, an ellipse, a polygon, a straight line, a polyline, and a spline curve, depending on a case.

Figure 16:
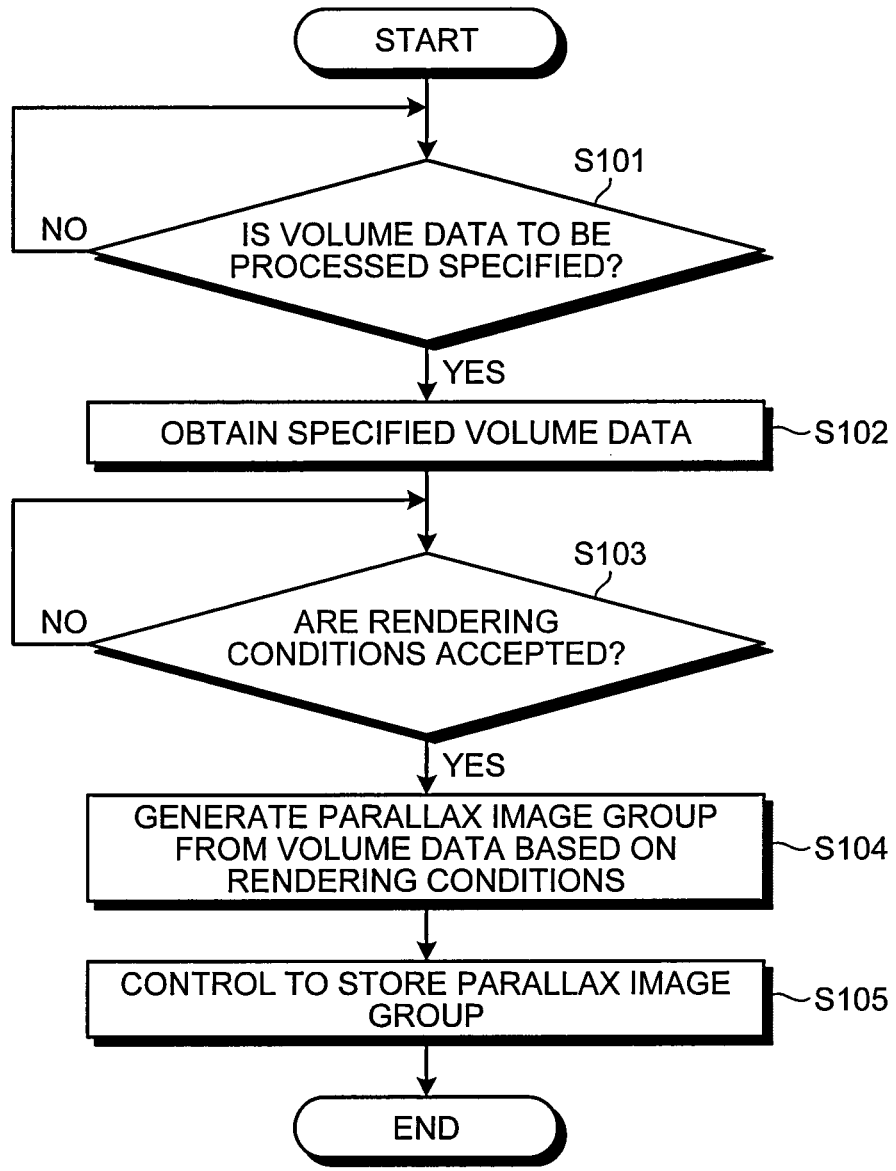
FIG. 16 is a diagram for explaining image storage processing of the image processing system according to the first embodiment.
Figure 17:
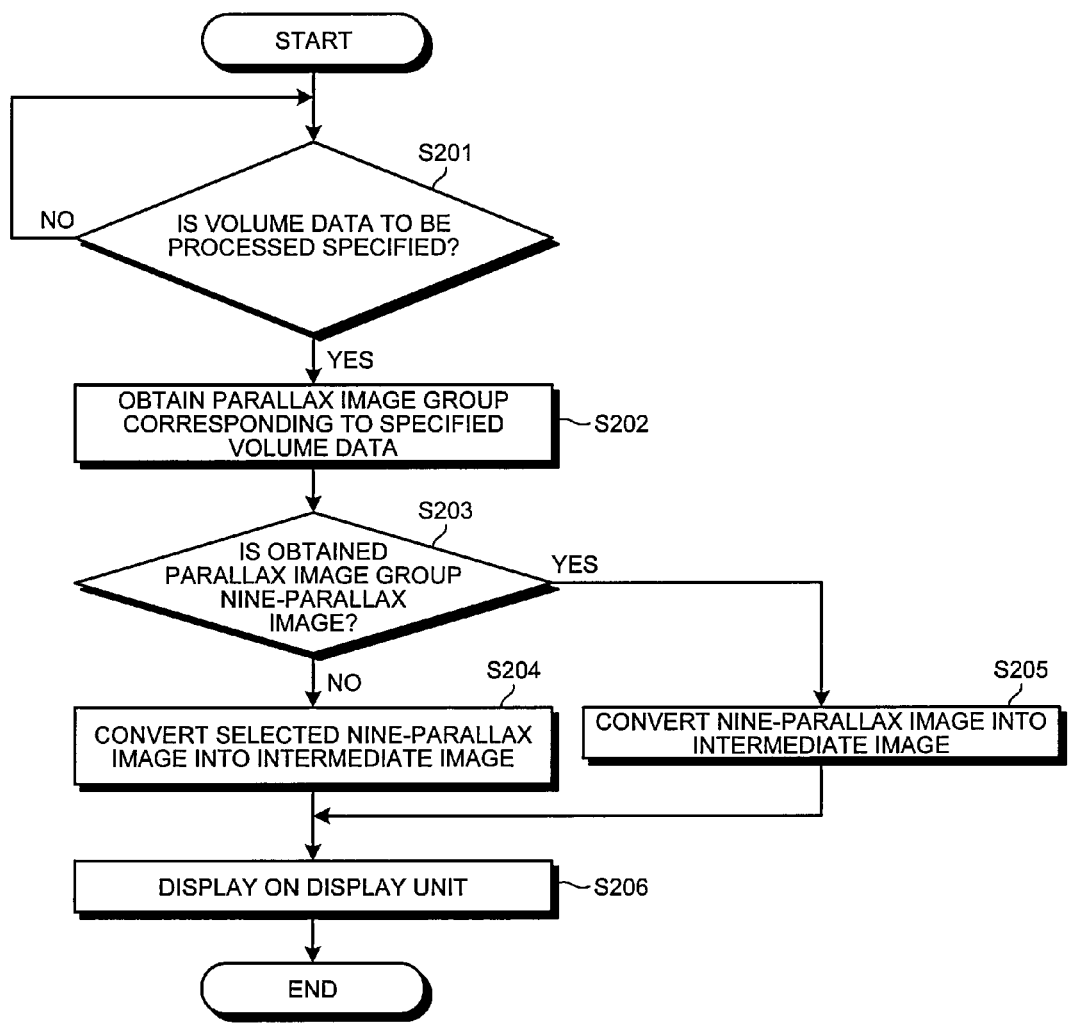
FIG. 17 is a diagram for explaining image display processing of the image processing system according to the first embodiment.

Next, description will be made of processing of the image processing system 1 according to the first embodiment using FIGS. 16 and 17. FIG. 16 is a diagram for explaining image storage processing of the image processing system according to the first embodiment. FIG. 17 is a diagram for explaining image display processing of the image processing system according to the first embodiment.

As illustrated in FIG. 16, the workstation 130 of the image processing system 1 according to the first embodiment determines whether volume data to be processed is specified (Step S101). Here, if no volume data is specified (No at Step S101), the workstation 130 waits until volume data is specified.

On the other hand, if volume data is specified (Yes at Step S101), the controller 135 obtains the specified volume data from the image storage device 120 (Step S102). Then, the controller 135 determines whether rendering conditions for the obtained volume data are accepted (Step S103). Here, the rendering conditions include the figure condition, the image count condition, and the viewpoint position condition described above in addition to the parallax angle, the segmentation condition, and others.

If no rendering conditions are accepted (No at Step S103), the controller 135 waits until rendering conditions are accepted. On the other hand, if rendering conditions are accepted (Yes at Step S103), the rendering processor 136 generates, under the control of the controller 135, a parallax image group from the volume data based on the rendering conditions (Step S104).

Then, the controller 135 controls the image storage device 120 so as to store the parallax image group (Step S105), and terminates the processing.

Thereafter, as illustrated in FIG. 17, the terminal device 140 of the image processing system 1 according to the first embodiment determines whether the operator has specified volume data to be processed (Step S201). Here, if no volume data is specified (No at Step S201), the terminal device 140 waits until volume data is specified.

On the other hand, if volume data is specified (Yes at Step S201), the controller 145 obtains the parallax image group corresponding to the specified volume data (Step S202), and determines whether the obtained parallax image group is a nine-parallax image (Step S203). The controller 145 stores the obtained parallax image group in the memory 144.

Here, if the obtained parallax image group is a nine-parallax image (Yes at Step S203), the controller 145 converts the nine-parallax image into an intermediate image (Step S205) and displays the image on the display unit 142 (Step S206), and then, the controller 145 terminates the processing.

On the other hand, if the obtained parallax image group is a group of 10 or more parallax images (No at Step S203), the controller 145 selects a nine-parallax image and converts it into an intermediate image (Step S204), and then, the controller 145 displays the image on the display unit 142 (Step S206) and terminates the processing. When performing the rotating display exemplified in FIG. 14, the controller 145 repeatedly executes the processes of Steps S204 and S206.

As has been described above, in the first embodiment, the parallax image group is generated from the volume data and stored in advance based on the various rendering conditions such as the first figure condition and the second figure condition. Thus, when a stereoscopic vision request is accepted, a stereoscopically viewable image group can be provided without performing the volume rendering processing in real-time. Accordingly, in the first embodiment, it is not necessary for the workstation 130 to have a high image processing capacity, and it is possible to reduce the load of processing required for generating the image for stereoscopic viewing from the three-dimensional medical image data.

Figure 18A:
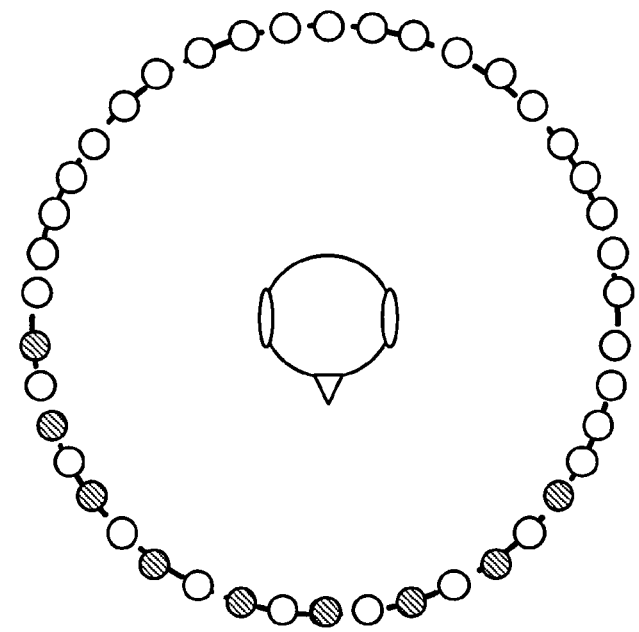
FIG. 18A and FIG. 18B are diagrams for explaining a first modification according to the first embodiment.
Figure 18B:
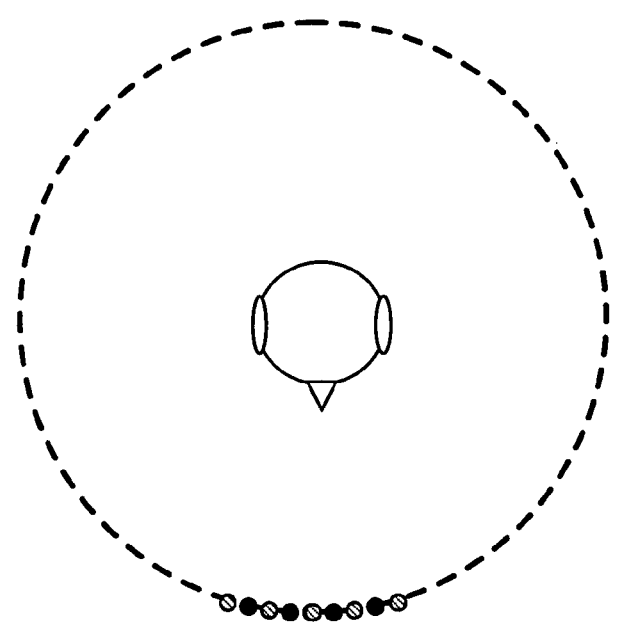

The first embodiment described above may have three modifications described below. The modifications of the first embodiment will be described below using FIGS. 18A to 20. FIGS. 18A and 18B are diagrams for explaining a first modification according to the first embodiment.

The first modification according to the first embodiment is for changing a stereoscopic effect of a stereoscopically viewed image in response to a request from the operator of the terminal device 140. For example, it is known that a nine-parallax image having a parallax angle of two degrees has a higher stereoscopic effect than that of a nine-parallax image having a parallax angle of one degree. Accordingly, the controller 145 according to the first modification changes the parallax angle of a group of as many images as the parallax number to be output to the display unit 142 for stereoscopic viewing. More specifically, the controller 145 changes the parallax angle between a predetermined parallax number of selected parallax images. For example, the input unit 141 is assumed to have a slide bar for adjusting the level of stereoscopic effect, and the position of the slide bar is assumed to correspond to the value of parallax angle.

Here, if the operator slides the bar to a position of "parallax angle of two degrees" for increasing the stereoscopic effect, the controller 145 determines that an image group having a parallax angle of two degrees can be selected from the entire circumferential data with a parallax angle of one degree. Then, as illustrated in FIG. 18A, the controller 145 selects every second parallax image up to a total of nine images from the entire circumferential data with a parallax angle of one degree so that the parallax angle is two degrees, and outputs the selected nine images to the display unit 142.

If the operator slides the bar to a position of "parallax angle of 0.5 degree" for reducing the stereoscopic effect, the controller 145 determines that a group of all images having a parallax angle of 0.5 degree cannot be selected from the entire circumferential data with a parallax angle of one degree. That is, the controller 145 determines that the parallax images in viewpoint positions indicated by black circles in FIG. 18B are not present. Accordingly, the controller 145 uses the interpolation function of the two-dimensional image processor 146. That is, as described above, the two-dimensional image processor 146 has the interpolation function that performs the interpolation processing to generate a new parallax image from two parallax images by using respective depth information of the two parallax images. A specific example of the interpolation processing performed by the two-dimensional image processor 146 will be described as follows. For example, when generating an image C located between an image A and an image B, the two-dimensional image processor 146 uses a mutual information method to calculate a warp field between the image A and the image B that indicates the direction from the image A to the image B. Then, the two-dimensional image processor 146 generates the image C by accumulating middle points of pixel vectors (halves of vectors from the image A to the image B) in the warp field to the image A. If the image C needs to be located not in the middle position but in a position, for example, at a ratio of 2 to 1 of an angle between the image A and the image B, the two-dimensional image processor 146 generates the image C by using pixels located in positions at a ratio of 2 to 1 of the vectors from the image A to the image B. If the angular distance between the image A and the image B is small, the two-dimensional image processor 146 may perform simple interpolation processing in which, without using the depth information, the two-dimensional image processor 146 adds pixel values of the image A to those of the image B and then halves the resultant pixel values.

The controller 145 controls the two-dimensional image processor 146 so as to generate, using the interpolation processing, each of the parallax images in the viewpoint positions indicated by the black circles in FIG. 18B from two already obtained parallax images adjacent thereto. That is, the two-dimensional image processor 146 performs the interpolation processing to generate a new parallax image corresponding to the viewpoint position indicated by the black circle by using respective depth information of the two parallax images generated by two viewpoints adjacent to the viewpoint position indicated by the black circle. As a result, the controller 145 controls to output the nine images achieving a parallax angle of 0.5 degree to the display unit 142.

In this manner, in the first modification according to the first embodiment, it is possible to change the stereoscopic effect of a stereoscopically viewed image in response to a request from the operator without performing the rendering processing again.

Figure 19A:
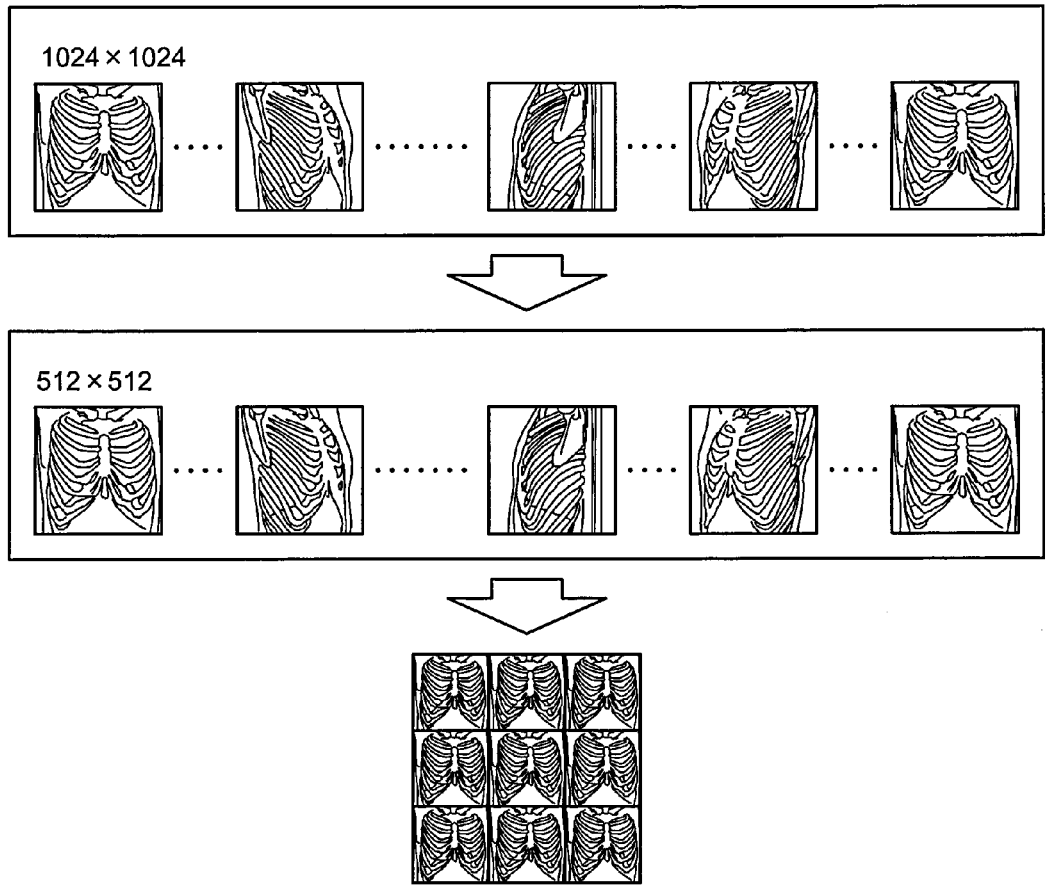
FIG. 19A and FIG. 19B are diagrams for explaining a second modification according to the first embodiment.
Figure 19B:
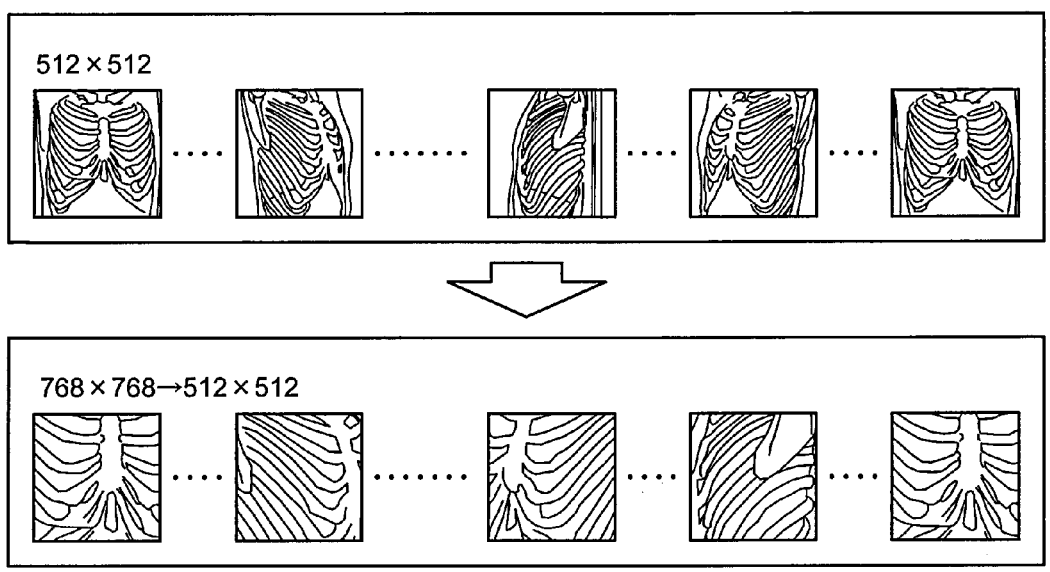

Next, a second modification according to the first embodiment will be described using FIGS. 19A and 19B. FIGS. 19A and 19B are diagrams for explaining a second modification according to the first embodiment.

In the second modification, the controller 135 that performs rendering control processing controls the rendering processor 136 so that a resolution of each image constituting the parallax image group is higher than a resolution of the stereoscopic display monitor (display unit 142) to which the images are output.

For example, the controller 135 obtains from the terminal device 140, in advance, information that the resolution of the display unit 142 is 512 pixels by 512 pixels. In such a case, the controller 135 instructs the rendering processor 136 to generate, for example, a volume rendering image having a resolution of 1024 pixels by 1024 pixels.

As a result, the controller 145 of the terminal device 140 obtains a nine-parallax image of 1024 pixels by 1024 pixels as illustrated in FIG. 19A. The controller 145 uses a scaling function included in the two-dimensional image processor 146 in order to output the obtained nine-parallax image to the display unit 142. For example, under the instruction of the controller 145, the two-dimensional image processor 146 performs the interpolation processing to calculate average values of pixel values of adjacent pixels, and thus, converts the nine-parallax image of 1024 pixels by 1024 pixels into a nine-parallax image of 512 pixels by 512 pixels as illustrated in FIG. 19A.

Then, as illustrated in FIG. 19A, the controller 145 converts the nine-parallax image of 512 pixels by 512 pixels into an intermediate image having a grid pattern, and outputs the image to the display unit 142.

Such a conversion from the high resolution image into the low resolution image can provide an effect described below. That is, when the operator refers to the nine-parallax image of 512 pixels by 512 pixels and then requests an enlarged display, the controller 145 instructs the two-dimensional image processor 146 to enlarge the nine-parallax image. Here, the terminal device 140 has the nine-parallax image of 1024 pixels by 1024 pixels stored in the memory 144.

For example, it is assumed that the area requested to be enlarged has a size of 768 pixels by 768 pixels in the original image. In such a case, the two-dimensional image processor 146 can generate a nine-parallax image for output by cutting out an area of 768 pixels by 768 pixels from the original image, and contracting the area to a size of 512 pixels by 512 pixels, as illustrated in FIG. 19B. The resolution of such a nine-parallax image is not reduced compared with the case in which the original image is a nine-parallax image of 512 pixels by 512 pixels.

In other words, in a third modification, a parallax image group having a high resolution is generated in advance, and thereby, when the stereoscopic image is displayed in an enlarged size on the monitor for stereoscopic viewing that is used for display, the image can be avoided to have a low resolution.

Figure 20:
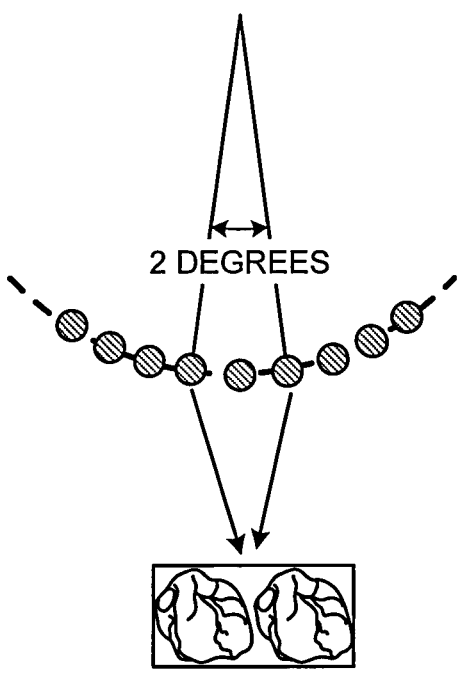
FIG. 20 is a diagram for explaining a third modification according to the first embodiment.

Next, the third modification according to the first embodiment will be described using FIG. 20. FIG. 20 is a diagram for explaining the third modification according to the first embodiment.

Although a case has been described above in which the display unit 142 is a nine-parallax monitor, the first embodiment can be applied to a case in which the display unit 142 is a two-parallax monitor which has been described using FIG. 2. For example, as illustrated in FIG. 20, it is assumed that the controller 145 obtains a nine-parallax image having a parallax angle of one degree as a parallax image group corresponding to volume data specified by the operator. In such a case, as illustrated in FIG. 20, the controller 145 selects, for example, a two-parallax image having a parallax angle of two degrees requested by the operator from the nine-parallax image, and outputs the two-parallax image to the display unit 142.

In this manner, the controller 135 controls to generate the parallax image group constituted by as many parallax images as or more parallax images than the maximum parallax number in advance, and thereby, the image for stereoscopic viewing can be displayed in accordance with stereoscopic specifications of the stereoscopic display monitor.

Note that the first embodiment and the modifications according to the first embodiment described above are applicable even when a plurality of pieces of volume data (4D data) along time series are to be processed. In such a case, the controller 135 generates a plurality of parallax image groups along time series. Then, the controller 135 stores the parallax image groups in the image storage device 120 in a corresponding manner to the 4D data. Then, the controller 145 obtains the parallax image groups corresponding to 4D data specified by the operator, and divides the obtained parallax image groups into individual stereoscopic images along time series. Then, the controller 145 displays the stereoscopic images as a stereoscopically viewable animation on the display unit 142.

In a second embodiment, description will be made of a data format of a parallax image group when being stored.

In the second embodiment, when performing storage control processing, the controller 135 of the workstation 130 performs control, based on standard specifications for sending and receiving medical images, so as to store a parallax image group in the image storage device 120 as video data in a video format.

More specifically, as has been described using FIG. 1, the controller 135 according to the second embodiment performs control, using the feature that the image processing system 1 is a PACS conforming to the DICOM standard serving as the standard specifications for medical images, so as to store the parallax image group in the image storage device 120 as video data in a format conforming to the DICOM standard.

In addition, the controller 135 according to the second embodiment attaches a private tag as supplementary information indicating that the image group stored as video data is an image group for stereoscopic viewing (parallax image group). With such a private tag attached, the controller 145 of the terminal device 140 according to the second embodiment obtains the video data of volume data specified by the operator from the image storage device 120, and based on the supplementary information attached to the obtained video data, determines whether the video data is the parallax image group.

For example, when the operator presses a "stereoscopic display button" provided on the input unit 131, the controller 145 of the terminal device 140 according to the second embodiment determines whether the obtained video data is convertible into data of a format for stereoscopic viewing. If the data is determined to be convertible, the controller 145 converts the video data into data of the format for stereoscopic viewing, and outputs the converted data to the display unit 142. On the other hand, if the data is determined to be unconvertible, the controller 145 dynamically displays the video data on the display unit 142.

Figure 21A:
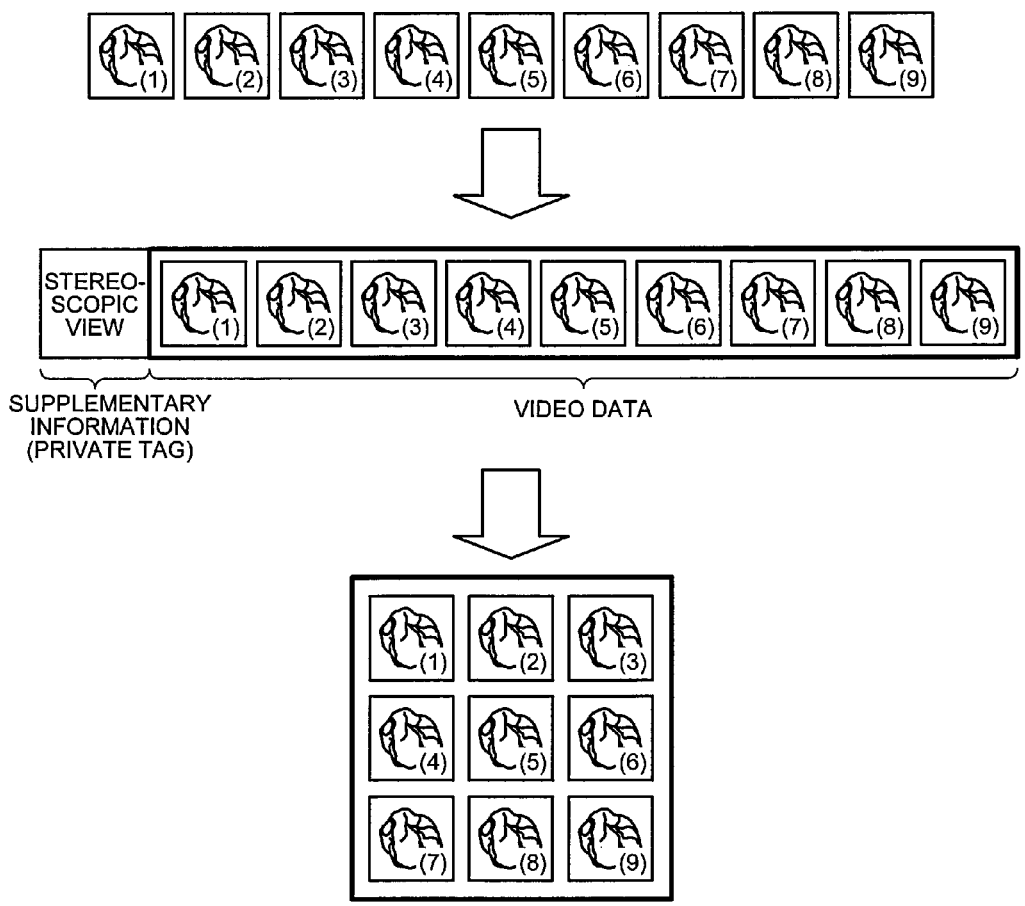

FIGS. 21A, 21B, 22, and 23 are diagrams each for explaining the private tag attached to the video data. For example, as illustrated in FIG. 21A, the controller 135 connects nine images into one long image, and thus provides a nine-parallax image as video data. Then, as illustrated in FIG. 21A, the controller 135 attaches a private tag "stereoscopic view" as supplementary information to the video data.

For example, when the stereoscopic display button is pressed, the controller 145 determines that the obtained video data is the parallax image group because the private tag "stereoscopic view" is attached. Then, the controller 145 converts the image group stored in the video data into a grid-like intermediate image, and outputs it to the display unit 142, as illustrated in FIG. 21A.

Figure 21B:
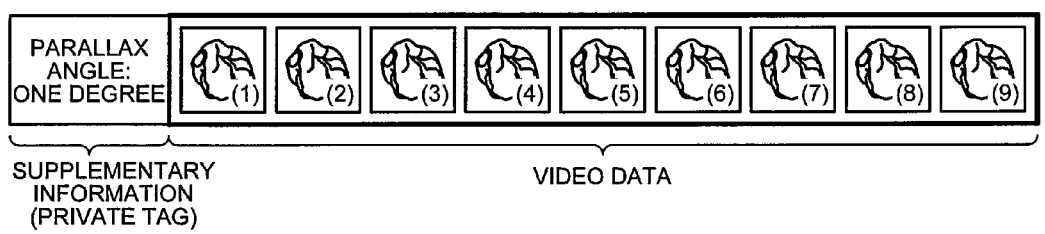

Alternatively, the information of the private tag attached to the nine-parallax image may be information on the parallax angle, as illustrated in FIG. 21B. For example, as illustrated in FIG. 21B, the controller 135 attaches "parallax angle: one degree" as the supplementary information to the video data. The controller 145 determines that the obtained video data is the image group for stereoscopic viewing (parallax image group) because the information on the parallax angle is attached.

The operator of the terminal device 140 may set in advance a threshold value for a parallax angle with which the operator can achieve stereoscopic viewing so as to avoid a problem that the operator cannot stereoscopically view the stereoscopic image displayed for stereoscopic viewing. For example, if the operator has set in advance information specifying "parallax angle: within two degrees", the controller 145 determines that the obtained video data is not stereoscopically viewable if, for example, a private tag indicating "parallax angle: five degrees" is attached to the data.

If, as illustrated in FIG. 22, the parallax image group is, for example, entire circumferential data composed of 360 images, the controller 135 treats the entire circumferential data of 360 images as one piece of video data. Then, as illustrated in FIG. 22, the controller 135 attaches a private tag "entire circumferential data" as supplementary information to the video data. For example, when the stereoscopic display button is pressed, the controller 145 determines that the obtained video data is the parallax image group because the private tag "entire circumferential data" is attached. Then, the controller 145 converts a nine-parallax image selected from the image group stored in the video data into a grid-like intermediate image, and outputs it to the display unit 142, as illustrated in FIG. 22.

Alternatively, when storing the parallax image group generated by the second figure condition described using FIG. 15, the controller 135 attaches a private tag illustrated in FIG. 23. More specifically, as illustrated in FIG. 23, the controller 135 attaches a private tag "stereoscopic view" and a private tag "entire circumferential data" as supplementary information to the video data. In addition, as illustrated in FIG. 23, the controller 135 inserts, as supplementary information for dividing the video data into pieces of entire circumferential data at each base point, "base point flag" in each position before the start of the entire circumferential data at each of the different base points.

Based on such supplementary information, the controller 145 determines the obtained video data is the parallax image group. Then, the controller 145 divides the video data at each of the flags, and after converting the stereoscopic images of the VE display method into images for stereoscopic viewing, outputs the converted images to the display unit 142.

In this manner, by using private tags, the parallax image group can be sent and received as DICOM standard compliant video data in the hospital where the PACS has been introduced. However, in the case of using private tags, it is necessary to add functions to allow the terminal device 140 serving as a viewer to identify the private tags. However, in order to add various private tag identification functions to the image processing system 1 which is operated as a PACS, the system needs to be changed.

Accordingly, the controller 135 performs control so as to treat the parallax image group as video data in a video format conforming to the DICOM standard, and after further attaching the supplementary information used in the standard specifications (DICOM standard) to the video data, to store the video data in the image storage device 120. Then, the controller 145 according to the second embodiment obtains the video data of volume data specified by the operator from the image storage device 120, and based on the supplementary information attached to the obtained video data, determines whether the video data is the parallax image group.

Figure 25:
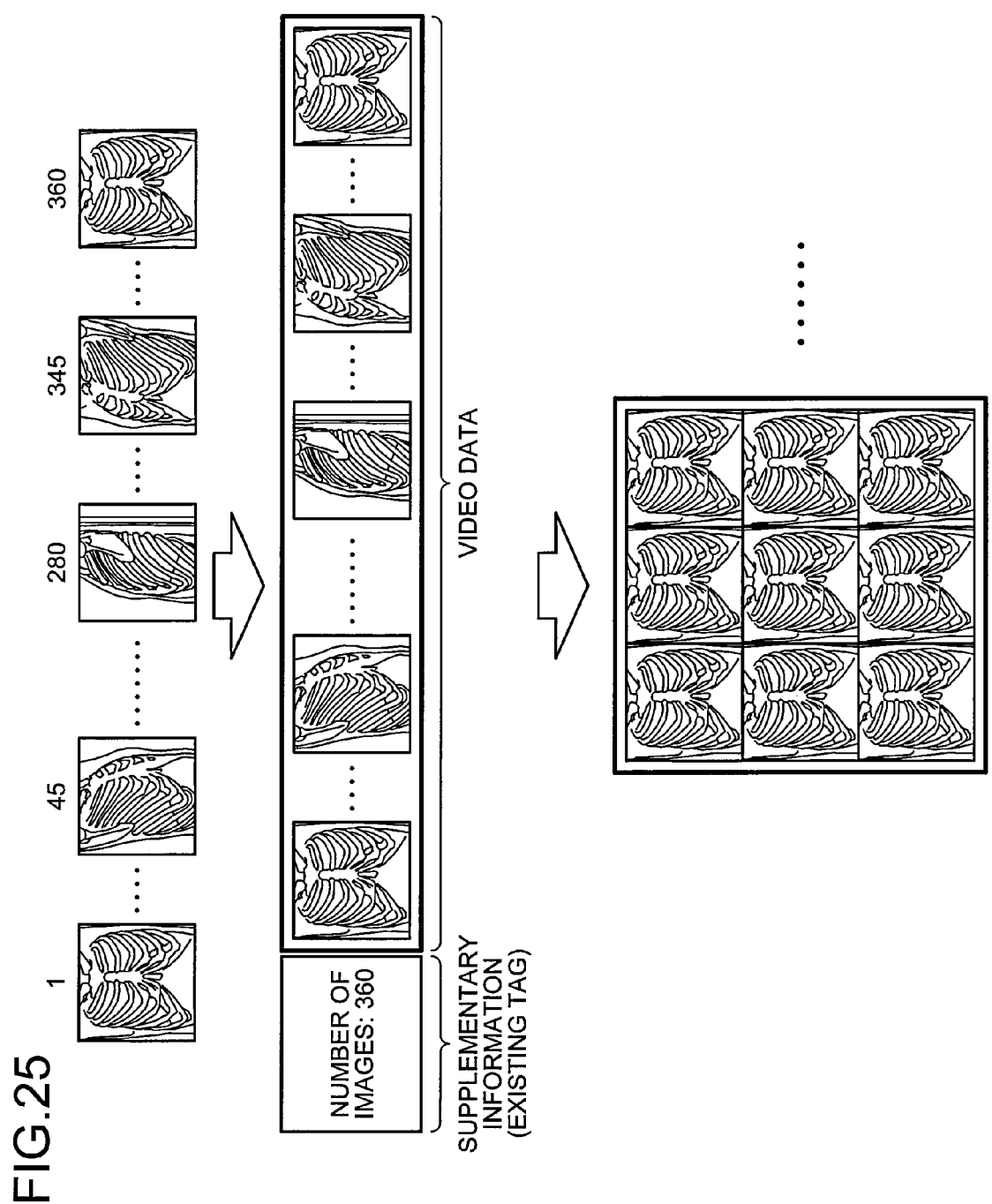

Using FIGS. 24 and 25, description will be made below of an example of DICOM standard compliant supplementary information that allows the video data determined to be a parallax image group. FIGS. 24 and 25 are diagrams for explaining the DICOM standard compliant supplementary information attached to the video data.

For example, as illustrated in FIG. 24, the controller 135 connects nine images into one long image, and thus provides a nine-parallax image as video data. Then, as illustrated in FIG. 24, the controller 135 attaches, to the video data, "number of images: 9" which is normally supplementary information as an existing tag given in the DICOM standard. For example, when the stereoscopic display button is pressed, the controller 145 determines that the obtained video data is the parallax image group because "number of images: 9" is attached. Then, the controller 145 converts the nine-parallax image stored in the video data into a grid-like intermediate image, and outputs it to the display unit 142.

Alternatively, if, as illustrated in FIG. 25, the parallax image group is entire circumferential data composed of 360 images, the controller 135 treats the entire circumferential data of 360 images as one piece of video data. Then, as illustrated in FIG. 25, the controller 135 attaches, to the video data, "number of images: 360" which is normally supplementary information as an existing tag given in the DICOM standard. For example, when the stereoscopic display button is pressed, the controller 145 determines that the obtained video data is the parallax image group because "number of images: 360" is attached. Then, the controller 145 converts a nine-parallax image selected from the parallax image group stored in the video data into a grid-like intermediate image, and outputs it to the display unit 142, as illustrated in FIG. 25. Further alternatively, the controller 145 converts a nine-parallax image sequentially selected from the parallax image group stored in the video data into a grid-like intermediate image, and sequentially outputs it to the display unit 142. Still alternatively, the controller 145 converts a nine-parallax image sequentially selected from continuous data in a certain range of the parallax image group stored in the video data into a grid-like intermediate image, and sequentially outputs it to the display unit 142. For example, the controller 145 sequentially selects a nine-parallax image from a parallax image group composed of first to 180th images of entire circumferential data composed of 360 images stored in the video data, and after converting the nine-parallax image into a grid-like intermediate image, sequentially outputs the intermediate image to the display unit 142.

Figure 26:
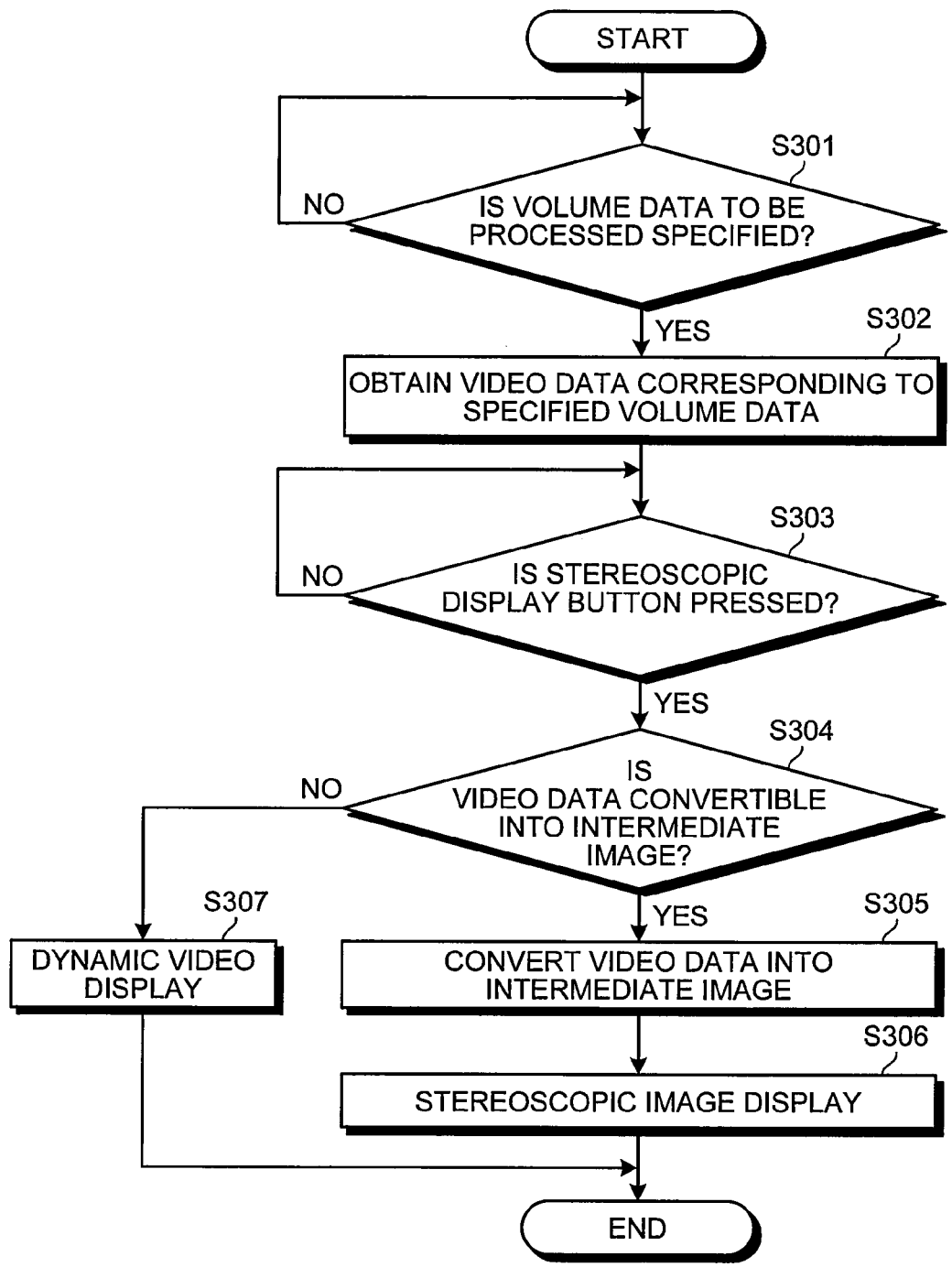
FIG. 26 is a diagram for explaining image display processing of an image processing system according to a second embodiment.

Next, description will be made of processing of the image processing system 1 according to the second embodiment using FIG. 26. FIG. 26 is a diagram for explaining image display processing of the image processing system according to the second embodiment. Image storage processing of the image processing system 1 according to the second embodiment is the same as that illustrated in FIG. 16 except that, at Step S105 described using FIG. 16, the controller 135 treats the parallax image group as DICOM standard compliant video data, and after attaching the supplementary information to the video data, stores the video data in the image storage device 120. Therefore, description of the image storage processing will be omitted.

As illustrated in FIG. 26, the terminal device 140 of the image processing system 1 according to the second embodiment determines whether the operator has specified volume data to be processed (Step S301). Here, if no volume data is specified (No at Step S301), the terminal device 140 waits until volume data is specified.

On the other hand, if volume data is specified (Yes at Step S301), the controller 145 obtains video data corresponding to the specified volume data (Step S302), and determines whether the stereoscopic display button is pressed (Step S303). Here, if the stereoscopic display button is not pressed (No at Step S303), the controller 145 waits until the stereoscopic display button is pressed.

On the other hand, if the stereoscopic display button is pressed (Yes at Step S303), the controller 145 refers to the supplementary information, and determines whether the video data is convertible into an intermediate image having a format for stereoscopic viewing (Step S304). Here, if the video data is determined to be unconvertible (No at Step S304), the controller 135 dynamically displays the obtained video data (Step S307), and terminates the processing.

On the other hand, if the video data is determined to be convertible (Yes at Step S304), the controller 135 converts the video data into the intermediate image (Step S305). Then, the controller 135 displays a stereoscopic image by outputting the intermediate image to the display unit 142 (Step S306), and terminates the processing.

As has been described above, in the second embodiment, the parallax image group is treated as DICOM standard compliant video data, and thereby, the stereoscopic image selected from the parallax image group can be displayed in the in the DICOM standard compliant in-hospital system that is currently most commonly used. In the second embodiment, it is also possible to determine, using the existing DICOM standard compliant tag, whether the video data is stereoscopically viewable. Therefore, the DICOM standard compliant in-hospital system that is currently most commonly used can be used, without any change, as a system for displaying the stereoscopic image selected from the parallax image group. A case has been described above in which pressing the stereoscopic display button starts the determination processing by the controller 145. However, the second embodiment may be a case in which the determination processing by the controller 145 is not triggered by operation of the stereoscopic display button, but started when the video data is obtained. In such a case, in the terminal device 140 equipped with an ordinary DICOM standard compliant viewer, the video data that is determined by the controller 145 to be unconvertible is identified as an animation and is dynamically displayed. A case has also been described above in which the parallax image group is treated as DICOM standard compliant video data. However, the second embodiment may be a case in which, for example, the data, such as the entire circumferential data, composed of 360 images is treated as DICOM standard compliant data composed of 360 still images that serves as standardized data compliant with the DICOM standard. In such a case, the controller 135 attaches, for example, an existing tag of "number of images: 360" to data including the DICOM still image data of 360 images. Then, the controller 145 selects a nine-parallax image from the DICOM still image data of 360 images, and outputs the nine-parallax image to the display unit 142. For example, when the stereoscopic display button is pressed, the controller 145 determines that the still image data group is the parallax image group because the existing tag of "number of images: 360" is attached to the data including the DICOM still image data of 360 images, and selects and outputs to the display unit 142 the nine-parallax image.

The second embodiment described above may have the modifications described below. That is, as described in the first embodiment, the image processing system 1 can also process 4D data, and the parallax image groups along time series generated under the control of the controller 135 can be treated as DICOM standard compliant video data.

First, as described in the first embodiment, if a plurality of pieces of volume data are generated along time series, the controller 135 controls the rendering processor 136 so as to generate the parallax image groups along time series from the pieces of volume data.

Then, in the modification according to the second embodiment, the controller 135 treats the parallax image groups generated by the rendering processor 136 as DICOM standard compliant video data in a video format. Here, also in the modification according to the second embodiment, private tags or existing tags can be attached to the video data as supplementary information.

Figure 27A:
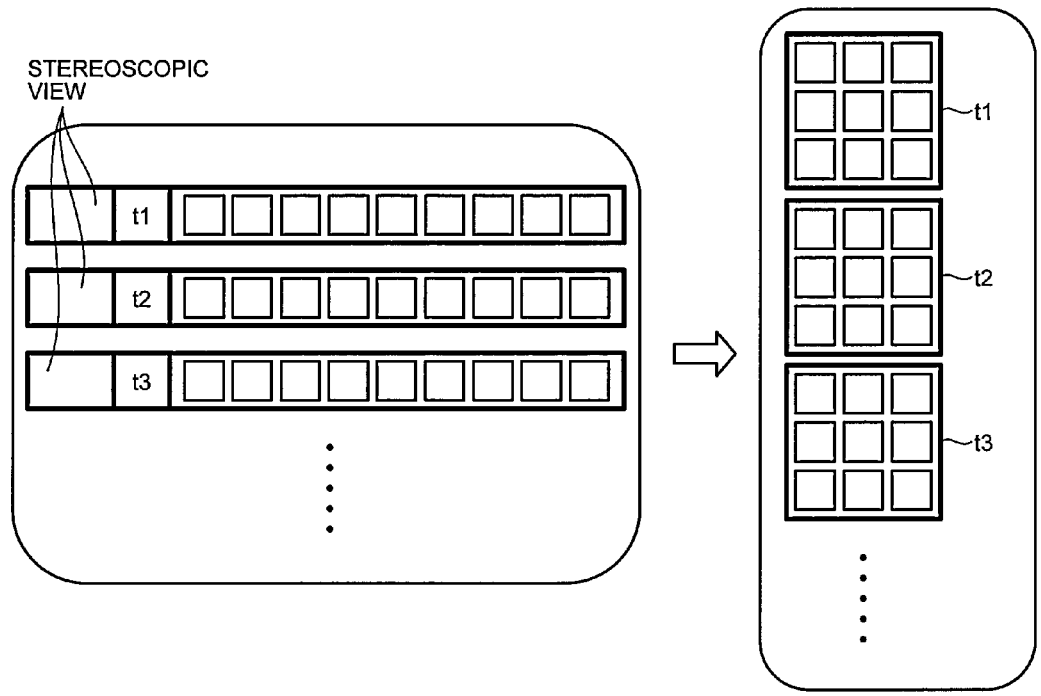
FIG. 27A and FIG. 27B are diagrams for explaining a private tag attached to video data in a modification according to the second embodiment.
Figure 27B:
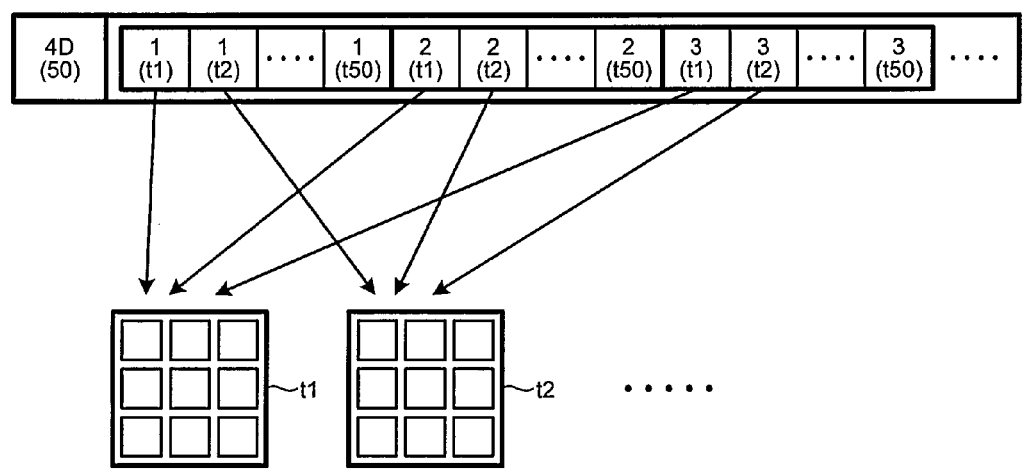

First, using FIGS. 27A and 27B, description will be made of examples of a private tag that is attached when nine-parallax image groups along time series are generated based on the rendering conditions described using FIG. 8B. FIGS. 27A and 27B are diagrams each for explaining the private tag attached to the video data in the modification according to the second embodiment. For example, as illustrated in FIG. 27A, the controller 135 treats each of a plurality of nine-parallax images along time series as video data. Moreover, the controller 135 attaches a private tag "stereoscopic view" to each piece of the video data.

The controller 135 also attaches time information as an existing tag to each piece of the video data. Here, the time information is a time when volume data serving as a generation source of the video data is photographed, and is, for example, information of time measured in units of milliseconds. For example, the controller 135 attaches to each piece of the video data an existing tag "'time: t1', 'time: t2', 'time: t3', . . . ". Such a video data group is stored by the storage control of the controller 135 in the image storage device 120 in a corresponding manner to the 4D data which is a generation source.

Then, the controller 145 collectively obtains the video data group corresponding to 4D data specified by the operator, and determines that the video data group is stereoscopically viewable because the private tag "stereoscopic view" is attached to every piece of the obtained video data. Moreover, the controller 145 determines that the video data group is the parallax image groups along time series for animation display because the existing tag attached to the obtained video data group indicates, for example, time measured in units of milliseconds.

Then, as illustrated in FIG. 27A, the controller 145 converts the video data group into a plurality of intermediate images along the time series of "'time: t1', 'time: t2', 'time: t3', . . . ", and outputs the intermediate images to the display unit 142.

Alternatively, the controller 135 treats a plurality of nine-parallax images along time series as one piece of video data. For example, as illustrated in FIG. 27B, the controller 135 treats 50 nine-parallax images along time series as one piece of video data. Note, however, that the controller 135 divides the 50 nine-parallax images "'time: t1', 'time: t2', 'time: t3', . . . , 'time: t50'" at each viewpoint position.

Then, the controller 135 arranges the parallax images of "time: t1" to "time: 50" for viewpoint (1) along the time series (refer to "1(t1), 1(t2), 1(t3), . . . , 1(t50)" in FIG. 27B). In the same manner, the controller 135 arranges the parallax images of "time: t1" to "time: 50" for viewpoint (2) along the time series (refer to "2(t1), 2(t2), 2(t3), . . . , 2(t50)" in FIG. 27B). In the same manner, the controller 135 arranges the parallax images of "time: t1" to "time: 50" for viewpoint (3) along the time series (refer to "3(t1), 3(t2), 3(t3), . . . , 3(t50)" in FIG. 27B). The controller 135 applies such sorting processing to viewpoints (4) to (9) in the same manner.

Then, the controller 135 attaches a private tag "4D (50)" representing a parallax image group for animation display to the video data. Note that the number 50 of the private tag is information indicating that 50 nine-parallax images along time series are stored as 4D data.

Then, the controller 145 obtains video data corresponding to 4D data specified by the operator, and determines that the video data is the parallax image groups that are stereoscopically viewable and used for animation display because the private tag "4D (50)" is attached to the obtained video data.

Then, as illustrated in FIG. 27B, the controller 145 converts the video data into a plurality of intermediate images along the time series of "'time: t1', 'time: t2', 'time: t3', . . . ", and outputs the intermediate images to the display unit 142.

However, as described above, in order to add various private tag identification functions to the image processing system 1 which is operated as a PACS, the system needs to be changed.

Figure 28:
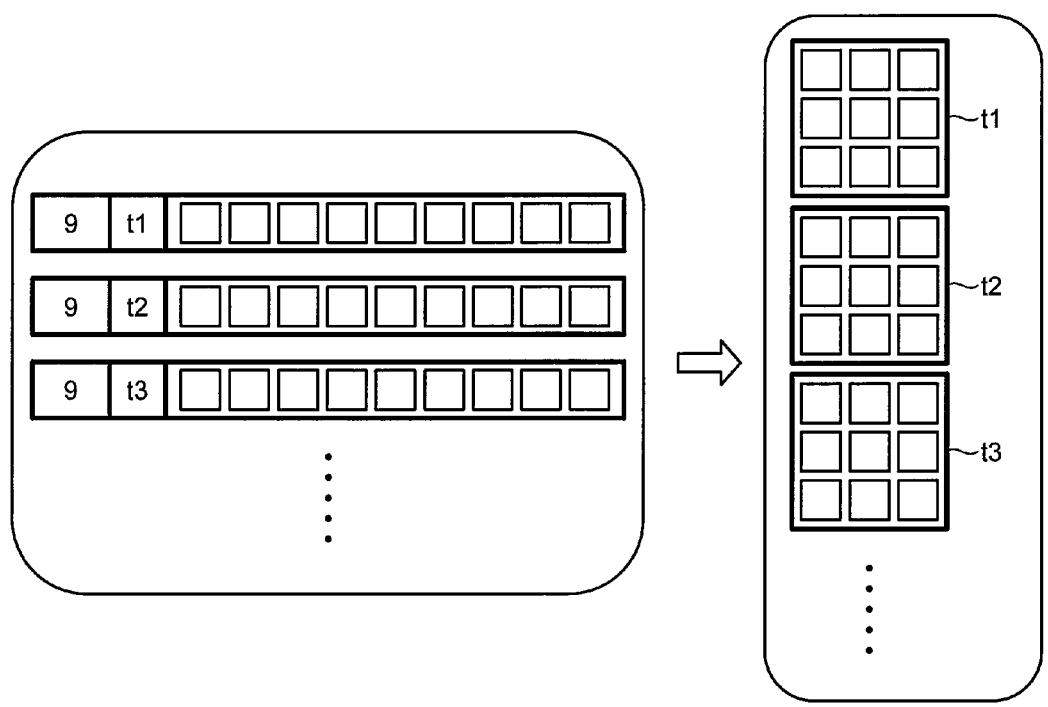
FIG. 28 is a diagram for explaining DICOM standard compliant supplementary information attached to the video data in the modification according to the second embodiment.

Accordingly, also in the present modification, controller 135 performs control so as to attach the DICOM standard compliant supplementary information (existing tag) to the video data and store the video data in the image storage device 120. FIG. 28 is a diagram for explaining the DICOM standard compliant supplementary information attached to the video data in the modification according to the second embodiment.

For example, as illustrated in FIG. 20, the controller 135 treats each of the nine-parallax images along time series as video data. Moreover, the controller 135 attaches "9" representing the number of images as an existing tag to each piece of the video data. Furthermore, the controller 135 attaches time information as an existing tag to each piece of the video data. For example, the controller 135 attaches to each piece of the video data an existing tag "'time: t1', 'time: t2', 'time: t3', . . . ". Such a video data group is stored by the storage control of the controller 135 in the image storage device 120 in a corresponding manner to the 4D data which is a generation source.

Then, the controller 145 obtains video data of 4D data specified by the operator from the image storage device 120, and based on the supplementary information attached to the obtained video data, determines whether the video data is the parallax image groups along time series for animation display.

The controller 145 determines the video data to be stereoscopically viewable because an existing tag indicating that the number of images is 9 is attached to every piece of the obtained video data. Moreover, the controller 145 determines that the video data group is the parallax image groups along time series for animation display because the existing tag attached to the obtained video data group indicates time measured in units of milliseconds.

Then, as illustrated in FIG. 28, the controller 145 converts the video data into a plurality of intermediate images along the time series of "'time: t1', 'time: t2', 'time: t3', . . . ", and outputs the intermediate images to the display unit 142. Note that the description made using FIGS. 27A, 27B, and 28 can be applied to the case in which the parallax image group is the entire circumferential data composed of 360 images.

In this manner, in the modification according to the second embodiment, the DICOM standard compliant in-hospital system that is currently most commonly used can be used, without any change, as a system for displaying the stereoscopic images even in the case of treating 4D data.

In the embodiments described above, description has been made of the case in which the workstation 130 performs the generation control and the storage control of the parallax image group with the controller 135 while the terminal device 140 performs the control for obtaining and displaying the stereoscopic image with the controller 145. However, the embodiment is not limited to this case. The embodiment may be, for example, a case in which the workstation 130 performs the control for obtaining and displaying the parallax image group in addition to the generation control and the storage control of the parallax image group. The embodiment may also be a case in which the medical diagnostic imaging apparatus 110 and the terminal device 140 perform the generation control and the storage control of the parallax image group, and also the control for obtaining and displaying the parallax image group.

Furthermore, the embodiment may be a case in which the medical diagnostic imaging apparatus 110 performs the generation control and the storage control of the parallax image group while the workstation 130 and the terminal device 140 perform the control for obtaining and displaying the parallax image group.

In the embodiments described above, description has also been made of the case in which the parallax image group is stored into the image storage device 120. However, the embodiment is not limited to this case. The embodiment may be, for example, a case in which the device that has performed the generation control of the parallax image group controls storage thereof into a memory of the device itself. In such a case, the terminal device 140 obtains the parallax image group, for example, from the workstation 130.

In other words, the processes of the rendering processor 136, the controller 135, the controller 145, and the image storage device 120 described in the above embodiments can be configured by being distributed and integrated in a functional or physical manner in any units according to various loads and use conditions of devices included in the image processing system 1. In addition, all or any part of the processing functions executed by each of the devices can be achieved by a CPU and a program analyzed and executed by the CPU, or can be implemented as hardware by a wired logic.

The image processing method described in the above embodiments can be realized by executing a preliminarily prepared image processing program with a computer such as a personal computer or a workstation. The image processing program can be distributed through a network such as the Internet. The program can also be executed by being recorded on a computer-readable recording medium, such as a hard disk, a flexible disk (FD), a compact disk read only memory (CD-ROM), a magneto-optical disk (MO), a digital versatile disk (DVD), or a Blu-ray (registered trademark) Disc, and by being read out from the recording medium by the computer.

As described above, with the first embodiment, the modification according to the first embodiment, the second embodiment, and the modification according to the second embodiment, it is possible to reduce the load of processing required for generating an image for stereoscopic viewing from three-dimensional medical image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing system, comprising:
a plurality of stereoscopic display devices, each configured to enable a stereoscopic image constituted by using a corresponding predetermined parallax number of parallax images to be stereoscopically viewed so that the plurality of stereoscopic display devices have a corresponding plurality of predetermined parallax numbers; and
an image processing apparatus that comprises:
a rendering processor configured to apply rendering processing to volume data serving as three-dimensional medical image data;
a rendering processing controller configured to control, before accepting a request for a stereoscopic view of the volume data, the rendering processor so as to generate, from the volume data, a parallax image group composed of at least a maximum parallax number of parallax images, the maximum parallax number being a maximum of the plurality of predetermined parallax numbers corresponding to the plurality of stereoscopic display devices; and
a storage controller configured to store, in a memory, the parallax image group that includes at least the maximum parallax number of the parallax images generated by the rendering processor, wherein
each of the stereoscopic display devices is configured to display the stereoscopic image constituted by selecting the corresponding predetermined parallax number of parallax images corresponding to each of the stereoscopic display devices out of the parallax image group that includes at least the maximum parallax number of the parallax images stored in the memory, and
the rendering processing controller controls the rendering processor to generate the parallax image group by setting at least a predetermined parallax number of viewpoints for performing the rendering processing, based on a straight line or a curve forming a figure having a predetermined shape.

2. The image processing system according to claim 1, further comprising a display controller configured to perform control so as to obtain, from the memory, the predetermined parallax number of parallax images out of the parallax image group generated from volume data specified by an operator, the predetermined parallax number of parallax images corresponding to one of the plurality of stereoscopic display devices with which display control is performed, and to display the stereoscopic image constituted by using the obtained predetermined parallax number of parallax images on the stereoscopic display device with which the display control is performed.

3. The image processing system according to claim 2, wherein the display controller is configured to perform control so as to sequentially display more than one of the stereoscopic images on the stereoscopic display device with which the display control is performed, by sequentially selecting, from the memory, the predetermined parallax number of parallax images corresponding to the stereoscopic display device with which the display control is performed.

4. The image processing system according to claim 2, wherein the display controller is configured to change a parallax angle between selected parallax images equal in number to the predetermined parallax number.

5. The image processing system according to claim 2, wherein the rendering processing controller is configured to treat the parallax image group as standardized data standardized in a format based on standard specifications for sending and receiving medical images while the storage controller is configured to further perform control so as to attach supplementary information used in the standard specifications to the standardized data and store the resulting data in the memory, and
the display controller is configured to obtain from the memory the standardized data of the volume data specified by the operator, and to determine, based on the supplementary information attached to the obtained standardized data, whether the standardized data is the parallax image group.

6. The image processing system according to claim 5, wherein the rendering processing controller is configured to treat the parallax image group as video data in a video format based on the standard specifications while the storage controller is configured to further perform control so as to attach the supplementary information used in the standard specifications to the video data and store the resulting data in the memory, and
the display controller is configured to obtain from the memory the video data of the volume data specified by the operator, and to determine, based on the supplementary information attached to the obtained video data, whether the video data is the parallax image group.

7. The image processing system according to claim 6, wherein the rendering processing controller is configured, if a plurality of pieces of volume data are generated along time series, to control the rendering processor so as to generate a plurality of parallax image groups along time series from the pieces of volume data, and to treat the parallax image groups generated by the rendering processor as the video data in the video format used in the standard specifications while the storage controller is configured to further perform control so as to attach the supplementary information used in the standard specifications to the video data and store the resulting data in the memory, and
the display controller is configured to obtain from the memory the video data of the pieces of volume data specified by the operator, and to determine, based on the supplementary information attached to the obtained video data, whether the video data is the parallax image groups along time series for animation display.

8. The image processing system according to claim 1, wherein the rendering processing controller is configured to set the figure having the predetermined shape so that the viewpoints are located outside a rendering area serving as an area to be rendered in the volume data, and is configured to control the rendering processor to generate the parallax image group based on the straight line or the curve forming the figure having the predetermined shape thus set.

9. The image processing system according to claim 8, wherein the rendering processing controller is configured to set at least the predetermined parallax number of viewpoints for performing the rendering processing along the straight line or the curve forming the figure having the predetermined shape.

10. The image processing system according to claim 8, wherein the rendering processing controller is configured to set at least the predetermined parallax number of viewpoints for performing the rendering processing along a tangent line at a point set on the straight line or the curve forming the figure having the predetermined shape.

11. The image processing system according to claim 8, wherein the rendering processing controller is configured to set the viewpoints for performing the rendering processing along each of tangent line directions at a plurality of points set on the straight line or the curve forming the figure having the predetermined shape.

12. The image processing system according to claim 1, wherein the rendering processing controller is configured to set the figure having the predetermined shape so that the viewpoints are located in a rendering area serving as an area to be rendered in the volume data, and is configured to control the rendering processor to generate the parallax image group based on the straight line or the curve forming the figure having the predetermined shape thus set.

13. The image processing system according to claim 1, wherein the rendering processing controller is configured to set more than one of the figures each having the predetermined shape.

14. The image processing system according to claim 1, wherein the rendering processing controller is configured to control the rendering processor so that a resolution of each image constituting the parallax image group is higher than a resolution of the stereoscopic display device with which display control is performed.

15. An image processing apparatus coupled to a plurality of stereoscopic display devices, each capable of displaying a stereoscopic image constituted by using a corresponding predetermined parallax number of parallax images, so that the plurality of stereoscopic display devices have a corresponding plurality of predetermined parallax numbers, the apparatus comprising:
   a rendering processor configured to apply rendering processing to volume data serving as three-dimensional medical image data;
   a rendering processing controller configured to control, before accepting a request for a stereoscopic view of the volume data, the rendering processor so as to generate, from the volume data, a parallax image group composed at least a maximum parallax number of parallax images, the maximum parallax number being a maximum of the plurality of predetermined parallax numbers corresponding to the plurality of stereoscopic display devices; and
   a storage controller configured to store, in a memory, the parallax image group that includes at least the maximum parallax number of the parallax images generated by the rendering processor, wherein
   each of the plurality of stereoscopic display devices is configured to display the stereoscopic image constituted by selecting the corresponding predetermined parallax number of parallax images corresponding to each of the stereoscopic display devices out of the parallax image group that includes at least the maximum parallax number of the parallax images stored in the memory, and
   the rendering processing controller controls the rendering processor to generate the parallax image group by setting at least a predetermined parallax number of viewpoints for performing the rendering processing, based on a straight line or a curve forming a figure having a predetermined shape.

16. An image processing method, comprising:
   a step, by an image processing apparatus coupled to a plurality of stereoscopic display devices, each capable of displaying a stereoscopic image constituted by using a predetermined parallax number of parallax images, so that the plurality of stereoscopic display devices have a corresponding plurality of predetermined parallax numbers, of controlling, before accepting a request for a stereoscopic view of the volume data, a rendering processor configured to apply rendering processing to volume data serving as three-dimensional medical image data, so as to generate, from the volume data, a parallax image group composed of at least a maximum parallax number of parallax images, the maximum parallax number being a maximum of the plurality of predetermined parallax numbers corresponding to the plurality of stereoscopic display devices;
   storing, in a memory, the parallax image group that includes at least the maximum parallax number of the parallax images generated by the rendering processor; and
   a step, by each of the plurality of stereoscopic display devices, of displaying the stereoscopic image constituted by selecting the corresponding predetermined parallax number of parallax images corresponding to each of the stereoscopic display devices out of the parallax image group that includes at least the maximum parallax number of the parallax images stored in the memory,
   wherein the image processing apparatus controls the rendering processor to generate the parallax image group by setting at least a predetermined parallax number viewpoints for performing the rendering processing, based on a straight line or a curve forming a figure having a predetermined shape.

\* \* \* \* \*